(12) United States Patent
Periana et al.

(10) Patent No.: US 11,814,348 B2
(45) Date of Patent: Nov. 14, 2023

(54) OXIDIZING LIQUID MEDIA FOR CHEMICAL TRANSFORMATIONS

(71) Applicants: University of Florida Research Foundation, Incorporated, Gainesville, FL (US); Hyconix, Inc., Chicago, IL (US)

(72) Inventors: Roy A. Periana, Jupiter, FL (US); Brian G. Hashiguchi, Naperville, IL (US); Michael M. Konnick, Aurora, IL (US)

(73) Assignees: University of Florida Research Foundation, Incorporated, Gainesville, FL (US); Hyconix, Inc., Chicago, IL (US)

( * ) Notice: Subject to any disclaimer, the term of this patent is extended or adjusted under 35 U.S.C. 154(b) by 496 days.

(21) Appl. No.: 16/616,604

(22) PCT Filed: May 25, 2018

(86) PCT No.: PCT/US2018/034698
§ 371 (c)(1),
(2) Date: Nov. 25, 2019

(87) PCT Pub. No.: WO2018/218171
PCT Pub. Date: Nov. 29, 2018

(65) Prior Publication Data
US 2021/0163503 A1    Jun. 3, 2021

Related U.S. Application Data

(60) Provisional application No. 62/511,173, filed on May 25, 2017, provisional application No. 62/654,133, filed on Apr. 6, 2018, provisional application No. 62/654,119, filed on Apr. 6, 2018.

(51) Int. Cl.
| | |
|---|---|
| *C07C 5/50* | (2006.01) |
| *C07C 29/132* | (2006.01) |
| *C07C 29/50* | (2006.01) |
| *C07C 67/30* | (2006.01) |
| *C07F 5/00* | (2006.01) |
| C07C 31/20 | (2006.01) |
| C07C 69/63 | (2006.01) |

(52) U.S. Cl.
CPC ............. *C07C 5/50* (2013.01); *C07C 29/132* (2013.01); *C07C 29/50* (2013.01); *C07C 67/30* (2013.01); *C07F 5/00* (2013.01); C07C 31/202 (2013.01); C07C 31/205 (2013.01); C07C 69/63 (2013.01); C07C 2523/18 (2013.01); C07C 2531/04 (2013.01)

(58) Field of Classification Search
CPC ........ C07F 5/00; C07C 2531/04; C07C 29/50; C07C 5/50
See application file for complete search history.

(56) References Cited

U.S. PATENT DOCUMENTS

| | | |
|---|---|---|
| 4,112,241 A | 9/1978 | Okano et al. |
| 4,508,653 A | 4/1985 | Goel |
| 9,096,564 B2 | 8/2015 | Van Ogtrop et al. |

FOREIGN PATENT DOCUMENTS

| | | | | |
|---|---|---|---|---|
| DE | 108969 A1 | 10/1974 | | |
| RU | 2599828 C2 | 10/2016 | | |
| WO | WO2014/130987 | * 8/2014 | ............... | C07C 9/02 |
| WO | WO 2014/130987 A1 | 8/2014 | | |
| WO | WO2015/021126 | * 2/2015 | ............... | C10L 1/24 |
| WO | WO 2015/021126 A1 | 2/2015 | | |

OTHER PUBLICATIONS

LibreTexts ( https://chem.libretexts.org/@go/page/45234; downloaded on May 1, 2023, pp. 13.5.1-13.5.4).*
Russian Patent Office, Official Action in Russian Patent Application No. 2019143400 (dated Apr. 8, 2020).
Hashiguchi et al., Designing Catalysts for Functionalization of Unactivated C—H Bonds Based on the CH Activation Reaction, *Accounts Of Chemical Rese*, 45(6): 885-898 (Jun. 19, 2012).
European Patent Office, International Search Report and the Written Opinion in International Application No. PCT/US2018/034706 (dated Jul. 23, 2018).
European Patent Office, International Search Report and the Written Opinion in International Application No. PCT/US2018/034698 (dated Sep. 6, 2018).
European Patent Office, International Search Report and the Written Opinion in International Application No. PCT/US2018/034717 (dated Oct. 24, 2018).

* cited by examiner

*Primary Examiner* — Pancham Bakshi
(74) *Attorney, Agent, or Firm* — Leydig, Voit & Mayer, Ltd.

(57) ABSTRACT

Provided is an oxidizing composition, in which a liquid medium is substantially inert in the presence of an oxidizing electrophile contained in the liquid medium. The composition comprises (a) an oxidizing electrophile comprising a main group element in oxidized form and at least one conjugate anion of an oxygen acid; (b) a non-oxidizable liquid selected from a fluorinated hydrocarbon, a sulfone, a deactivated arene, a deactivated aliphatic, a deactivated heteroarene, a deactivated heteroaliphatic, and a combination thereof; and (c) optionally one or more salt additives. Further provided are a method of using the oxidizing composition to oxidize a substrate and a method of generating and/or regenerating an oxidizing electrophile comprising a main group element.

28 Claims, 10 Drawing Sheets

M = As, Sb, or Bi, n = 3, z = 4
M = Te or Se, n = 4, z = 5
M = Sn, n = 2, z = 3

| Entry | Substrate | Oxidant | [Oxidant] (mM) | Liquid Species | Additive | [Additive] (mM) | Temp. (°C) | Time (h) |
|---|---|---|---|---|---|---|---|---|
| 1 | Propane | Sb(TFA)$_3$/H$_2$O$_2$ | 100 | TFAH | TFA$_2$O/NaTFA | 637/100 | 180 | 3 |
| 2 | Propane | Na[Sb(OH)$_6$] | 100 | TFAH | TFA$_2$O | 637 | 180 | 17 |
| 3 | Propane | Sb(TFA)$_3$/H$_2$O$_2$ | 100 | TFAH | TFA$_2$O/C$_6$F$_5$CO$_2$H | 676/333 | 150 | 3 |
| 4 | Propane | Sb(TFA)$_3$/H$_2$O$_2$ | 300 | TFAH | TFA$_2$O/C$_6$F$_5$CO$_2$H | 707/1000 | 150 | 1 |
| 5 | Propane | Sb(TFA)$_3$/H$_2$O$_2$ | 100 | TFAH | TFA$_2$O/C$_6$H$_5$CO$_2$H | 500/100 | 150 | 3 |
| 6 | Propane | Sb(TFA)$_3$/H$_2$O$_2$ | 100 | TFAH | TFA$_2$O/Phthalic acid | 500/100 | 150 | 3 |
| 7 | Propane | Sb(TFA)$_3$/H$_2$O$_2$ | 100 | TFAH | TFA$_2$O/p-NO$_2$-C$_6$H$_4$CO$_2$H | 500/100 | 150 | 3 |
| 8 | Propane | Sb(TFA)$_3$/H$_2$O$_2$ | 100 | TFAH | TFA$_2$O/Pyrazine | 500/100 | 150 | 3 |
| 9 | Propane | Sb(TFA)$_3$/H$_2$O$_2$ | 100 | Et(TFA)$_2$/TFAH | TFA$_2$O/C$_6$F$_5$CO$_2$H | 500/100 | 150 | 3 |
| 10 | Propane | Sb(TFA)$_3$/H$_2$O$_2$ | 100 | DMS/TFAH | TFA$_2$O/C$_6$F$_5$CO$_2$H | 500/100 | 125 | 1 |
| 11 | Propane | Pb(OAc)$_4$ | 100 | HOAc | N/A | N/A | 130 | 3 |
| 12 | Propane | Pb(OAc)$_4$ | 100 | HOAc | NaOAc | 300 | 130 | 3 |
| 13 | Propane | Pb(OAc)$_4$ | 100 | HOAc | H$_2$O | 1000 | 130 | 3 |
| 14 | Propane | Pb(OAc)$_4$ | 100 | HOAc | H$_2$SO$_4$ | 275 | 130 | 3 |
| 15 | Propane | Pb(TFA)$_4$ | 100 | TFAH | N/A | N/A | 130 | 3 |
| 16 | Propane | Pb(TFA)$_4$ | 100 | TFAH | NaTFA | 300 | 130 | 3 |
| 17 | Propane | Pb(TFA)$_4$ | 100 | TFAH | H$_2$O | 1000 | 130 | 3 |
| 18 | Propane | I(TFA)$_3$ | 300 | TFAH | N/A | N/A | 180 | 2 |
| 19 | Propane | C$_6$F$_5$I(TFA)$_2$ | 100 | TFAH | N/A | N/A | 140 | 1 |
| 20 | Propane | C$_6$F$_5$I(TFA)$_2$ | 780 | TFAH | TFA$_2$O | 100 | 140 | 1 |
| 21 | Propane | C$_6$F$_5$I(TFA)$_2$ | 100 | AcOH | Ac$_2$O | 100 | 150 | 3 |
| 22 | Propane | C$_6$H$_3$I(CO$_2$)$_2$ | 100 | TFAH | N/A | N/A | 170 | 3 |
| 23 | Ethane | C$_6$F$_5$I(TFA)$_2$ | 780 | TFAH | TFA$_2$O | 100 | 140 | 1 |
| 24 | Ethane | Sb(TFA)$_3$/H$_2$O$_2$ | 100 | TFAH | TFA$_2$O/C$_6$F$_5$CO$_2$H | 500/100 | 150 | 3 |
| 25 | Ethane | [Sb(OMe)$_5$]$_2$ | 50 | TFAH | TFA$_2$O | 2360 | 150 | 4 |
| 26 | Ethane | Sb(TFA)$_3$/H$_2$O$_2$ | 50 | TFAH | TFA$_2$O | 687 | 150 | 4 |
| 27 | Methane | Sb(TFA)$_3$/H$_2$O$_2$ | 100 | TFAH | TFA$_2$O/C$_6$F$_5$CO$_2$H | 500/100 | 150 | 3 |
| 28 | BuTFA | C$_6$F$_5$I(TFA)$_2$ | 250 | TFAH | TFA$_2$O | 100 | 150 | 3 |

FIG. 4A

| Entry | Substrate | Oxidant | Oxidant Conversion | Liquid Species | Additive | [Additive] (mM) | Temp. (°C) |
|---|---|---|---|---|---|---|---|
| 29 | Benzylalcohol | Pb(OAc)$_4$ | N/A | TCE | N/A | N/A | 100 |
| 30 | Benzylalcohol | Pb(OAc)$_4$ | N/A | Nitrobenzene | N/A | N/A | 100 |
| 31 | Phenylacetylene | C$_6$F$_5$I(TFA)$_2$ | 100 | 1,3-(CF$_3$)$_2$-Benzene | N/A | N/A | 100 |
| 32 | Benzaldehyde | C$_6$F$_5$I(TFA)$_2$ | 48 | 1,3-(CF$_3$)$_2$-Benzene | N/A | N/A | 100 |
| 33 | Benzylalcohol | C$_6$F$_5$I(TFA)$_2$ | 100 | 1,3-(CF$_3$)$_2$-Benzene | N/A | N/A | 100 |
| 34 | Phenylacetylene | C$_6$F$_5$I(TFA)$_2$ | 100 | Sulfolane | TFAH | 1000 | 150 |
| 35 | Benzaldehyde | C$_6$F$_5$I(TFA)$_2$ | 4 | Sulfolane | TFAH | 1000 | 150 |
| 36 | Benzylalcohol | C$_6$F$_5$I(TFA)$_2$ | 100 | Sulfolane | TFAH | 1000 | 150 |
| 37 | Phenylacetylene | Hg(TFA)$_2$ | N/A | Sulfolane | TFAH | 1000 | 150 |
| 38 | Benzaldehyde | Hg(TFA)$_2$ | N/A | Sulfolane | TFAH | 1000 | 150 |
| 39 | Phenylacetylene | Pb(OAc)$_4$ | N/A | Sulfolane | TFAH | 1000 | 150 |
| 40 | Benzaldehyde | Pb(OAc)$_4$ | N/A | Sulfolane | TFAH | 1000 | 150 |
| 41 | Benzylalcohol | Pb(OAc)$_4$ | N/A | Sulfolane | TFAH | 1000 | 150 |
| 42 | Benzaldehyde | C$_6$F$_5$I(TFA)$_2$ | 1 | Sulfolane | MsOH/H$_2$O | 500/250 | 150 |
| 43 | Toluene | C$_6$F$_5$I(TFA)$_2$ | 87 | Sulfolane | MsOH/H$_2$O | 500/250 | 150 |
| 44 | Benzaldehyde | Pb(OAc)$_4$ | N/A | Sulfolane | MsOH/H$_2$O | 500/250 | 150 |
| 45 | Benzaldehyde | Te(OH)$_6$ | N/A | Sulfolane | AcOH | 1000 | 150 |
| 46 | Benzaldehyde | Te(OH)$_6$ | N/A | Sulfolane | AcOH/MsOH | 1000/600 | 150 |
| 47 | Benzylalcohol | Te(OH)$_6$ | N/A | Sulfolane | AcOH/MsOH | 1000/600 | 150 |
| 48 | Benzaldehyde | Te(OH)$_6$ | N/A | Sulfolane | AcOH/MNB-H | 1000/600 | 150 |
| 49 | Benzaldehyde | Te(OH)$_6$ | N/A | Sulfolane | AcOH/Ac$_2$O | 1000/700 | 150 |
| 50 | Benzaldehyde | Te(OH)$_6$ | N/A | Sulfolane | AcOH/MsOH/Ac$_2$O | 1000/600/700 | 150 |
| 51 | Benzylalcohol | Te(OH)$_6$ | N/A | Sulfolane | AcOH/MsOH/Ac$_2$O | 1000/600/700 | 150 |

FIG. 4B

| Entry | Substrate | Oxidant | Oxidant Conversion | Liquid Species | Additive | [Additive] (mM) | Temp. (°C) |
|---|---|---|---|---|---|---|---|
| 52 | Benzaldehyde | Te(OH)$_6$ | N/A | Sulfolane | AcOH/MNB-H/Ac$_2$O | 1000/600/700 | 150 |
| 53 | Benzylalcohol | Te(OH)$_6$ | N/A | Sulfolane | AcOH/MNB-H/Ac$_2$O | 1000/600/700 | 150 |
| 54 | Benzaldehyde | Te(OH)$_6$ | N/A | Sulfolane | AcOH/MNB-H | 600/600 | 200 |
| 55 | Benzylalcohol | Te(OH)$_6$ | N/A | Sulfolane | AcOH/MNB-H | 600/600 | 200 |
| 56 | Benzaldehyde | Te(OH)$_6$ | N/A | Sulfolane | AcOH/MNB-H/MsOH | 600/600/600 | 200 |
| 57 | Benzylalcohol | Te(OH)$_6$ | N/A | Sulfolane | AcOH/MNB-H/MsOH | 600/600/600 | 200 |
| 58 | Toluene | C$_6$F$_5$I(TFA)$_2$ | 15 | Sulfolane | TFAH | 1000 | 150 |
| 59 | Anisole | C$_6$F$_5$I(TFA)$_2$ | 98 | Sulfolane | TFAH | 1000 | 150 |
| 60 | Benzyl Ether | C$_6$F$_5$I(TFA)$_2$ | 3 | Sulfolane | TFAH | 1000 | 150 |
| 61 | Toluene | C$_6$F$_5$I(TFA)$_2$ | 45 | Sulfolane | MsOH/TFAH | 1000/1000 | 150 |
| 62 | Anisole | C$_6$F$_5$I(TFA)$_2$ | 99 | Sulfolane | MsOH/TFAH | 1000/1000 | 150 |
| 63 | Benzyl Ether | C$_6$F$_5$I(TFA)$_2$ | 4 | Sulfolane | MsOH/TFAH | 1000/1000 | 150 |
| 64 | Toluene | Pb(OAc)$_4$ | N/A | Sulfolane | MsOH | 1000 | 150 |
| 65 | Benzyl Ether | Pb(OAc)$_4$ | N/A | Sulfolane | MsOH | 1000 | 150 |
| 66 | Toluene | Pb(OAc)$_4$ | N/A | Sulfolane | MsOH/TFAH | 1000/1000 | 150 |
| 67 | Anisole | Pb(OAc)$_4$ | N/A | Sulfolane | MsOH/TFAH | 1000/1000 | 150 |
| 68 | Benzyl Ether | Pb(OAc)$_4$ | N/A | Sulfolane | MsOH/TFAH | 1000/1000 | 150 |
| 69 | Toluene | Pb(OAc)$_4$ | N/A | Sulfolane | TFAH | 1000 | 150 |
| 70 | Anisole | Pb(OAc)$_4$ | N/A | Sulfolane | TFAH | 1000 | 150 |
| 71 | Benzyl Ether | Pb(OAc)$_4$ | N/A | Sulfolane | TFAH | 1000 | 150 |
| 72 | Toluene | Sb(TFA)$_3$/H$_2$O$_2$ | N/A | TFAH | TFA$_2$O/C$_6$F$_5$CO$_2$H | 1000/200 | 100 |
| 73 | Benzene | Sb(TFA)$_3$/H$_2$O$_2$ | N/A | TFAH | TFA$_2$O/C$_6$F$_5$CO$_2$H | 1000/200 | 150 |

FIG. 4C

| Entry | Major Product | % Major Product | Minor Product | % Minor Product | Total (% Yield) |
|---|---|---|---|---|---|
| 1 | iPrTFA | 4 | | 0 | 4 |
| 2 | iPrTFA | 4 | | 0 | 4 |
| 3 | 1,2-Pr(TFA)$_2$ | 30 | | 0 | 30 |
| 4 | 1,2-Pr(TFA)$_2$ | 30 | iPrTFA | 12 | 42 |
| 5 | 1,2-Pr(TFA)$_2$ | 1 | | 0 | 1 |
| 6 | 1,2-Pr(TFA)$_2$ | 2 | | 0 | 2 |
| 7 | 1,2-Pr(TFA)$_2$ | 6 | | 0 | 6 |
| 8 | iPrTFA | 4 | | 0 | 4 |
| 9 | iPrTFA | 8 | 1,2-Pr(TFA)$_2$ | 2 | 10 |
| 10 | 1,2-Pr(TFA)$_2$ | 10 | | 0 | 10 |
| 11 | iPrOAc | 25 | 1,2-Pr(OAc)$_2$ | 7 | 32 |
| 12 | iPrOAc | 35 | 1,2-Pr(OAc)$_2$ | 20 | 55 |
| 13 | iPrOAc | 37 | 1,2-Pr(OAc)$_2$ | 22 | 59 |
| 14 | iPrOAc | 10 | 1,2-Pr(OAc)$_2$ | 6 | 16 |
| 15 | iPrTFA | 55 | 1,2-Pr(TFA)$_2$ | 36 | 91 |
| 16 | iPrTFA | 53 | 1,2-Pr(TFA)$_2$ | 40 | 93 |
| 17 | iPrTFA | 54 | 1,2-Pr(TFA)$_2$ | 34 | 88 |
| 18 | iPrTFA | 40 | 1,2-Pr(TFA)$_2$ | 2 | 42 |
| 19 | iPrTFA | 35 | 1,2-Pr(TFA)$_2$ | 12 | 47 |
| 20 | 1,2-Pr(TFA)$_2$ | 48 | iPrTFA | 26 | 74 |
| 21 | 1,2-Pr(X)$_2$ X = OAc or TFA | 53 | iPr(X) X = OAc or TFA | 34 | 87 |
| 22 | iPrTFA | 50 | nPrTFA | 3 | 53 |
| 23 | EtTFA | 67 | Et(TFA)$_2$ | 13 | 80 |
| 24 | EtTFA | 8 | Et(TFA)$_2$ | 2 | 10 |
| 25 | EtTFA | 14 | Et(TFA)$_2$ | 9 | 32 |
| 26 | EtTFA | 14 | Et(TFA)$_2$ | 8 | 30 |
| 27 | MeTFA | 4 | | 0 | 4 |
| 28 | 1,4-Bu(TFA)$_2$ | 5 | | 0 | 5 |

FIG. 4D

| Entry | Major Product | % Major Product | Minor Product | % Minor Product | Total (% Yield) |
|---|---|---|---|---|---|
| 29 | Benzaldehyde | 70 | Benzoic acid | 6 | 76 |
| 30 | Benzaldehyde | 53 |  | 0 | 53 |
| 31 | Phenacyl-TFA | 28 |  | 0 | 28 |
| 32 | Arylation products | 20 | Arylation products | 22 | 42 |
| 33 | Benzaldehyde | 45 |  | 0 | 45 |
| 34 | Phenacyl-TFA | 71 | PhCH(OH)CH(TFA)CH₂-TFA isomer | 17 | 88 |
| 35 | Benzoic acid | 7 |  | 0 | 7 |
| 36 | Benzaldehyde | 48 |  | 0 | 48 |
| 37 | PhCH(TFA)CH(TFA)OH or PhCH(OH)CH(TFA)CH₂-TFA | 12 |  | 0 | 12 |
| 38 | Benzaldehyde | 8 |  | 0 | 8 |
| 39 | Phenacyl-TFA | 16 |  | 16 | 32 |
| 40 | Benzoic acid | 17 |  | 0 | 17 |

FIG. 4E

| Entry | Major Product | % Major Product | Minor Product | % Minor Product | Total (% Yield) |
|---|---|---|---|---|---|
| 41 | Benzaldehyde | 63 | | 0 | 63 |
| 42 | Benzoic acid | 35 | | 0 | 35 |
| 43 | Arylation products | 68 | Arylation products | 14 | 82 |
| 44 | Benzoic acid | 52 | | 0 | 52 |
| 45 | Benzoic acid | 17 | | 0 | 17 |
| 46 | Benzoic acid | 32 | | 0 | 32 |
| 47 | Benzaldehyde | 10 | | 0 | 10 |
| 48 | Benzoic acid | 7 | | 0 | 7 |
| 49 | Benzoic acid | 32 | | 0 | 32 |
| 50 | Benzoic acid | 27 | | 0 | 27 |
| 51 | Benzaldehyde | 10 | | 0 | 10 |
| 52 | Benzoic acid | 13 | | 0 | 13 |
| 53 | Benzaldehyde | 7 | | 0 | 7 |
| 54 | Benzoic acid | 22 | | 0 | 22 |
| 55 | Benzaldehyde | 15 | | 0 | 15 |
| 56 | Benzoic acid | 19 | | 0 | 19 |
| 57 | Benzaldehyde | 5 | | 0 | 5 |
| 58 | p-Tolyl acetate | 7 | Arylation products | 5 | 12 |
| 59 | p-Anisoyl acetate | 70 | Arylation products | 17 | 87 |

FIG. 4F

| Entry | Major Product | % Major Product | Minor Product | % Minor Product | Total (% Yield) |
|---|---|---|---|---|---|
| 60 | Benzaldehyde | 33 | Benzoic acid | 2 | 35 |
| 61 | p-Tolyl acetate | 31 | Arylation products | 12 | 43 |
| 62 | p-Anisoyl acetate | 72 | Arylation products | 21 | 93 |
| 63 | Benzaldehyde | 33 | Benzoic acid | 2 | 35 |
| 64 | p-Tolyl acetate | 12 | | 0 | 12 |
| 65 | Benzaldehyde | 9 | Benzoic acid | 2 | 11 |
| 66 | p-Tolyl acetate | 2 | | 0 | 2 |
| 67 | p-Anisoyl acetate | 5 | | 0 | 5 |
| 68 | Benzaldehyde | 9 | Benzoic acid | 1 | 10 |
| 69 | p-Tolyl acetate | 2 | | 0 | 2 |
| 70 | p-Anisoyl acetate | 43 | | 0 | 43 |
| 71 | Benzaldehyde | 8 | Benzoic acid | 2 | 10 |
| 72 | p-Tolyl acetate | 35 | | 0 | 35 |
| 73 | Phenyl acetate | 40 | | 0 | 40 |

FIG. 4G

| Entry | Electrophile | [Electrophile] (mM) | Oxidant | Liquid Medium | Additive | [Additive] (mM) | Temp. (°C) | Soluble Pre-oxidation | Soluble Post-oxidation | After Anhydride Treatment |
|---|---|---|---|---|---|---|---|---|---|---|
| 74 | Sb(OAc)₃ | 100 | CH₃CO₃H | HOAc | N/A | N/A | 4 | Y | N | N |
| 75 | Sb(OAc)₃ | 100 | CH₃CO₃H | HOAc | NaOAc | 300 | 4 | Y | Y | Y |
| 76 | Sb(TFA)₃ | 100 | 50% H₂O₂ | TFAH | N/A | N/A | 4 | Y | N | N |
| 77 | Sb(TFA)₃ | 100 | 50% H₂O₂ | TFAH | NaTFA | 100 | 4 | Y | Y | Y |
| 78 | Sb(TFA)₃ | 100 | 50% H₂O₂ | TFAH | Bipyrazine | 100 | 4 | Y | N | N |
| 79 | Sb(TFA)₃ | 100 | 50% H₂O₂ | TFAH | Pyrazine | 100 | 4 | Y | Y | Y |
| 80 | Sb(TFA)₃ | 100 | 50% H₂O₂ | TFAH | Perfluoropyridine | 100 | 4 | Y | Y | Y |
| 81 | Sb(TFA)₃ | 100 | 50% H₂O₂ | TFAH | C₆F₅CO₂H | 100 | 4 | Y | Y | Y |
| 82 | Sb(TFA)₃ | 100 | 50% H₂O₂ | TFAH | PNB-H | 100 | 4 | Y | Y | Y |
| 83 | Sb(OAc)₃ | 100 | 50% H₂O₂ | Sulfolane | HOAc | 500 | 60 | Y | N | N |
| 84 | Sb(PNB)₃ | 100 | 50% H₂O₂ | Sulfolane | PNB-H | 500 | 60 | Y | Y | Y |
| 85 | Te(OH)₆ | 200 | N/A | Sulfolane | AcOH | 600 | 25 | Y | N/A | N/A |
| 86 | Te(OH)₆ | 200 | N/A | Sulfolane | AcOH/DNB-H | 300/300 | 25 | Y | N/A | N/A |
| 87 | Te(OH)₆ | 200 | N/A | Sulfolane | DNB-H | 600 | 25 | Y | N/A | N/A |
| 88 | Sn(OAc)₂ | 100 | 50% H₂O₂ | Nitrobenzene | AcOH | 400 | 25 | N | N | N |
| 89 | Sn(OAc)₂ | 100 | 50% H₂O₂ | Nitrobenzene | AcOH/MNB-H | 200/200 | 25 | Y | Y | Y |
| 90 | Sn(OAc)₂ | 100 | 50% H₂O₂ | Nitrobenzene | MNB-H | 400 | 25 | Y | Y | Y |
| 91 | Sn(OAc)₂ | 100 | 50% H₂O₂ | Sulfolane | AcOH | 400 | 25 | N | N | N |
| 92 | Sn(OAc)₂ | 100 | 50% H₂O₂ | Sulfolane | AcOH/MNB-H | 200/200 | 25 | Y | Y | Y |
| 93 | Sn(OAc)₂ | 100 | 50% H₂O₂ | Sulfolane | MNB-H | 400 | 25 | Y | Y | Y |
| 94 | Sn(OAc)₄ | 100 | N/A | Nitrobenzene | AcOH | 400 | 25 | N | N/A | N/A |
| 95 | Sn(OAc)₄ | 100 | N/A | Nitrobenzene | AcOH/MNB-H | 200/200 | 25 | Y | N/A | N/A |
| 96 | Sn(OAc)₄ | 100 | N/A | Nitrobenzene | MNB-H | 400 | 25 | Y | N/A | N/A |

FIG. 5

OXIDIZING LIQUID MEDIA FOR CHEMICAL TRANSFORMATIONS

CROSS-REFERENCE TO RELATED APPLICATIONS

This patent application is a U.S. national phase of International Patent Application No. PCT/US2018/034698, filed May 25, 2018, which claims the benefit of U.S. Provisional Patent Application 62/654,133, filed Apr. 6, 2018, U.S. Provisional Patent Application 62/654,119, filed Apr. 6, 2018, and U.S. Provisional Patent Application 62/511,173, filed May 25, 2017, the disclosures of which are incorporated herein by reference in their entireties for all purposes.

BACKGROUND OF THE INVENTION

Techniques for the efficient and low-cost oxidation of relatively unreactive small molecules, such as alkanes, are currently underdeveloped in the chemical industry. These small molecule feedstocks are highly abundant and readily accessible, yet, underutilized due to certain drawbacks. For example, during the conversion of methane to methanol, the homolytic C—H bond strength of methane is ~105 kcal/mol, whereas the homolytic bond strength of methanol is ~90 kcal/mol. Thus, it is common for the product of the oxidation process to be more reactive than the starting material. Generally, this unfavorable reactivity results in low selectivity to products and the formation of by-products formed by over-oxidation.

One common approach for the oxidation of relatively unreactive small molecules, such as alkanes, requires direct oxidation, in either the gas or liquid phase, and using oxygen or air as the terminal oxidant. Typically, this commercial process utilizes free radical pathways that also require the incorporation of a heterogeneous catalyst and high temperatures (e.g., greater than 600° C.). Due to elevated reaction temperatures and highly reactive free radical intermediates, this approach is often low yielding and/or lacks product selectivity.

Another approach for the oxidation of relatively unreactive small molecules requires using a metal catalyst in the presence of a superacid. Typically, the superacid is present in high concentration, and in many instances is present as the non-oxidizable liquid. Due to the necessity for large quantities of a superacid, this approach is not cost efficient. In addition, the reaction mixtures are generally corrosive, dangerous, and therefore, not feasible for an industrial scale process.

Thus, common techniques for the oxidation of relatively unreactive small molecules require harsh conditions and often result in low selectivity to products and the formation of by-products formed by over-oxidation. Accordingly, there remains a need for a mild and cost efficient process to convert these readily available small molecule feedstocks into useful products and chemical building blocks.

An oxidizing composition that can selectively oxidize difficult-to-oxidize alkanes and whose oxidizing potential can be adjusted by changing the environment around the main group oxidant represents a new class of selective oxidizing agents. Such an oxidizing composition can be used for the oxidation of a broad range of functional groups.

BRIEF SUMMARY OF THE INVENTION

The invention provides an oxidizing composition comprising, consisting essentially of, or consisting of: (a) an oxidizing electrophile comprising a main group element in oxidized form and at least one conjugate anion of an oxygen acid; (b) a non-oxidizable liquid selected from a fluorinated hydrocarbon, a sulfone, a deactivated arene, a deactivated aliphatic, a deactivated heteroarene, a deactivated heteroaliphatic, and a combination thereof; and (c) optionally one or more salt additives of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z. In the oxidizing composition, the non-oxidizable liquid is substantially inert in the presence of the oxidizing electrophile.

The invention also provides a process for oxidizing a substrate, comprising, consisting essentially of, or consisting of (a) contacting a substrate and (i) an oxidizing electrophile comprising a main group element in oxidized form, or (ii) an oxidant and a reduced form of the oxidizing electrophile, in a liquid medium comprising a non-oxidizable liquid and optionally one or more additives selected from an oxygen acid, a salt additive, a Lewis acid, and water, to provide an oxidized substrate and a reduced form of the oxidizing electrophile; and (b) optionally separating the oxidized substrate and the reduced form of the oxidizing electrophile.

The invention also provides a method of generating and/or regenerating an oxidizing electrophile comprising a main group element comprising: (a) providing a mixture comprising (i) a reduced form of an electrophile comprising a main group element, (ii) a liquid medium comprising a non-oxidizable liquid, and (iii) optionally one or more additives selected from an oxygen acid, a salt additive, a Lewis acid, and water, and (b) contacting the mixture with an oxidant to form the oxidized form of the electrophile comprising the main group element, wherein about 25% or less of the total mass of the oxidizing electrophile is an insoluble solid in the mixture.

BRIEF DESCRIPTION OF THE DRAWINGS

FIGS. 4A-4C are tables of exemplary reaction conditions for the procedure outlined in Example 7. FIGS. 4D-4G are tables of exemplary results for the procedure outlined in Example 7.

FIG. 5 is a table of reaction conditions and solubility results for Example 8.

DETAILED DESCRIPTION OF THE INVENTION

Figure 1:
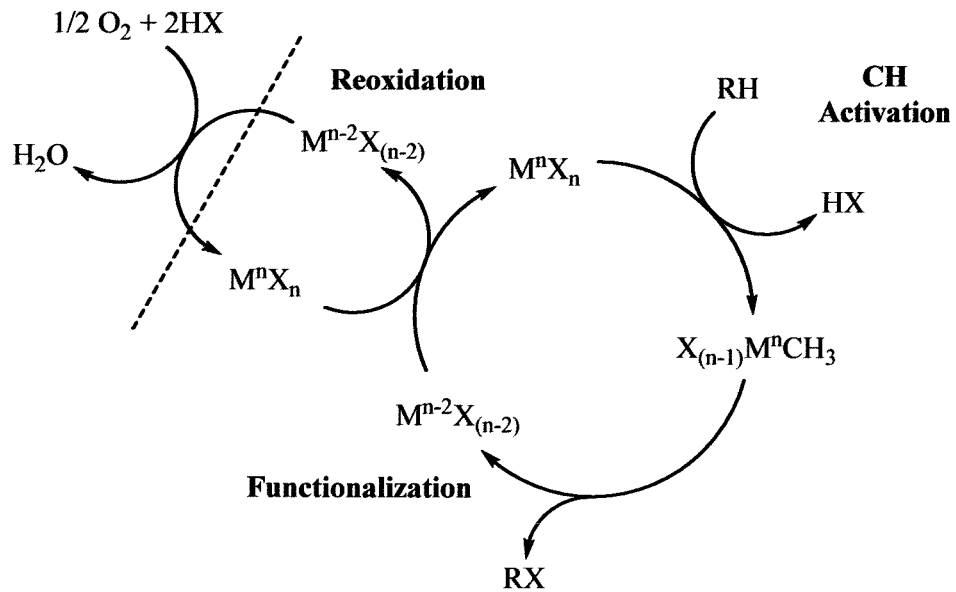
FIG. 1 illustrates an exemplary reaction cycle for the oxidation process. In the process, M used in the functionalization step can be the same or different as the M used in the reoxidation step.

The invention provides an oxidizing composition comprising, consisting essentially of, or consisting of: (a) an oxidizing electrophile comprising a main group element in oxidized form and at least one conjugate anion of an oxygen acid; (b) a non-oxidizable liquid selected from a fluorinated hydrocarbon, a sulfone, a deactivated arene, a deactivated aliphatic, a deactivated heteroarene, a deactivated heteroaliphatic, and a combination thereof; and (c) optionally one or more salt additives of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z; and wherein the non-oxidizable liquid is substantially inert in the presence of the oxidizing electrophile.

The oxidizing composition comprises an oxidizing electrophile and a non-oxidizable liquid. The non-oxidizable liquid can be any suitable liquid (e.g., fluid or solvent) such that the liquid is not consumed under the oxidizing conditions. If the liquid is oxidized (i.e. consumed), this results in increased cost both in terms of the loss of the liquid and in the formation of undesired by-products. Therefore, the liquid desirably is "substantially inert" in the presence of the oxidizing electrophile. That is to say, the oxidizing electrophile selectively oxidizes a substrate in favor of the non-oxidizable liquid when the oxidizing composition comes in contact with a substrate. Due to the strong oxidizing potential of the oxidizing electrophile, the ability of the non-oxidizable liquid to remain "substantially inert" allows for the oxidizing composition to oxidize a number of substrates, which traditionally, are considered difficult to oxidize, e.g., alkanes. These and other advantages of the invention, as well as additional inventive features, will be apparent from the description of the invention provided herein.

As used herein, "substantially inert" refers to a liquid (e.g., fluid or solvent) that maintains greater than about 80% stability in the presence of the oxidizing electrophile, such as measured by the retention of the non-oxidizable liquid peaks in a $^1$H Nuclear Magnetic Resonance (NMR) spectrum, relative to a standard. In certain embodiments, the liquid can maintain greater than about 85% stability in the presence of the oxidizing electrophile, for example, greater than about 90% stability in the presence of the oxidizing electrophile, greater than about 92% stability in the presence of the oxidizing electrophile, greater than about 94% stability in the presence of the oxidizing electrophile, greater than about 95% stability in the presence of the oxidizing electrophile, greater than about 98% stability in the presence of the oxidizing electrophile, or greater than about 99% stability in the presence of the oxidizing electrophile. Ideally, the liquid is totally inert to the oxidizing conditions but with strong oxidants, it can be expected that a small amount of liquid may be consumed or lost in subsequent recycle steps.

As used herein, the terms "liquid" or "liquid medium" refer to any medium that comprises a liquid. For example, the liquid or liquid medium can exist as a liquid-solid medium, a liquid-gas medium, a liquid-liquid medium, a liquid-gas-solid medium, etc. Accordingly, the liquid or liquid medium can be, for example, a solution, a gas-sparged liquid, a gel, a colloid, a slurry, a dispersion, an emulsion, or a combination thereof.

Hydrocarbons, such as alkanes, typically require harsh reaction conditions (e.g., free radical-based chemistry) to undergo chemical transformations, and traditional techniques tend to result in complex product mixtures that include over-oxidized products. In contrast to conventional techniques, the process, described herein, does not utilize harsh reaction conditions to oxidize the substrate. More particularly, the process does not oxidize the substrate by a free radical mechanism. Without wishing to be bound by any theory, it is believed that the mechanism by which the process converts a substrate to an oxidized substrate, occurs through an electrophilic C—H activation ("CHA") reaction. FIG. 1 illustrates an exemplary reaction cycle for the oxidation process.

The effectiveness of the process, described herein, is best viewed in terms of the oxidizing electrophile's ability to react selectively with a functionalized or unfunctionalized substrate to form an oxidized substrate (e.g., R—OY). Products generated from the direct oxidation of the relatively inert C—H bond are less reactive than the corresponding substrate; moreover, the groups (e.g., —OY) in the oxidized substrate (e.g., oxygenate) are more electron-withdrawing than the hydrogen in the corresponding C—H bond of a functionalized or unfunctionalized substrate (i.e., R—H). This oxidative process is advantageous because it typically generates products with high selectivity and high substrate conversion.

The oxidizing composition and associated processes effectively oxidize a substrate without the need for a superacid. Superacids are highly corrosive and require the need for specialized metallurgy throughout the process. They complicate the process and substantially increase cost. As used herein, a superacid is understood to mean an acid with an acidity greater than or equal to that of concentrated sulfuric acid, which has a Hammett acidity function ($H_0$) of −12. Examples of a superacid include concentrated (98%) sulfuric acid and trifluoromethanesulfonic acid ($CF_3SO_3H$), and fluorosulfuric acid ($HSO_3F$), both of which are about a thousand times stronger (i.e., have more negative $H_0$ values) than concentrated sulfuric acid. Thus, the oxidizing composition can contain superacid (e.g., more than 1 mol %, more than 5 mol %, more than 10 mol %, or more than 20 mol %), can be substantially free of superacid (e.g., 1 mol % or less, 0.9 mol % or less, 0.7 mol % or less, 0.5 mol % or less, 0.3 mol % or less, 0.1 mol % or less), or may not contain superacid (e.g., below the level of detection). In preferred embodiments, the oxidizing composition is substantially free of superacid (e.g., 1 mol % or less, 0.9 mol % or less, 0.7 mol % or less, 0.5 mol % or less, 0.3 mol % or less, 0.1 mol % or less) or does not contain superacid. Preferably, the oxidizing composition does not contain superacid.

In some embodiments, the oxidizing electrophile is of the formula $M^{+n}X_pL_q$, wherein M is a main group element cation in an oxidation state of n, X is the conjugate anion of an oxygen acid, L is a ligand, n is an integer from 2 to 6 (i.e., 2, 3, 4, 5, or 6), p is an integer from 1 to 6 (i.e., 1, 2, 3, 4, 5, or 6), and q is an integer from 0 to 5 (i.e., 0, 1, 2, 3, 4, or 5). The oxidizing electrophile of the formula $M^{+n}X_pL_q$ can have any suitable net charge. For example, the oxidizing electrophile of the $M^{+n}X_pL_q$ can have a net charge of +5, +4, +3, +2, or +1, or a neutral net charge. In certain embodiments, the oxidizing electrophile of the formula $M^{+n}X_pL_q$ is a neutral species. Without wishing to be bound to any particular theory, the reactive species $[M^{+n}X_p]$ can have up to q number of ligands (L) to either balance the net charge of $[M^{+n}X_p]$ and/or solvate the remaining charge of $[M^{+n}X_p]$.

The oxidizing electrophile comprises a main group element. The main group element (M) typically includes elements in the post-transition metal and non-metal groups of the periodic table and include, for example, elements with atomic numbers 31, 32, 33, 34, 35, 49, 50, 51, 52, 53, 81, 82, and 83. In an embodiment, the term "main group element" typically refers to any element having filled 4d or 5d orbitals, which undergoes a net one- or two-electron change in oxidation state. Suitable main group elements include thallium, indium, lead, antimony, mercury, tin, selenium, tellurium, arsenic, cadmium, iodine, and bismuth. In some embodiments, the main group element is antimony, tellurium, bismuth, or arsenic. In some embodiments, the oxidizing electrophile comprises iodine. In further embodiments, the oxidizing electrophile comprises Sb(V), Te(VI), Te(IV), Bi(V), Se(VI), Se(IV), As(V), I(V), I(III), or Sn(IV).

The oxidizing electrophile comprises at least one conjugate anion of an oxygen acid. For example, the oxidizing electrophile can comprise 1, 2, 3, 4, 5, or 6 conjugate anions of an oxygen acid. As used herein, "oxygen acid" refers to any organic acid or inorganic acid which contains hydrogen, oxygen, and at least one other element, in which the protic hydrogen is attached to oxygen. Generally, the conjugate anion of an oxygen acid is selected from sulfite, sulfate, hydrogen sulfate, thiosulfate, nitrite, nitrate, phosphate, phosphite, hydrogen phosphate, dihydrogen phosphate, carbonate, hydrogen carbonate, oxalate, cyanate, isocyanate, chromate, dichromate, permanganate, carboxylate, sulfonate, borate, and any combination thereof.

In some embodiments, the conjugate anion of an oxygen acid is an electron-deficient alkoxide, aryloxide, or a combination thereof. As used herein, the term "electron-deficient alkoxide" refers to any alkoxide with at least one electron withdrawing substituent as described here. For example, the electron-deficient alkoxide can be trifluoroethoxide. As used herein, the term "aryloxide" refers to any oxide with an aryl group as described herein. For example, the electron-deficient aryloxide can be phenoxide with electron-withdrawing groups on the ring.

In some embodiments, the conjugate anion of an oxygen acid is selected from a carboxylate, a sulfate, a sulfonate, a phosphate, a borate, and a combination thereof. Typically, the carboxylate can be an aliphatic carboxylate (e.g., acetate), an aromatic carboxylate or a fluorinated carboxylate (e.g., trifluoroacetate (TFA)). Similarly, the sulfonate can be an aliphatic sulfonate (e.g., methanesulfonate), an aromatic sulfonate, or a fluorinated sulfonate (e.g., trifluoromethanesulfonate). The conjugate anion of the oxygen acid can be an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof. In some embodiments, the conjugate anion of the oxygen acid is trifluoroacetate, acetate, alkylsulfonate, phosphate, nitrate, sulfate, trifluoromethanesulfate, or fluorosulfate.

Accordingly, X of the formula $M^{+n}X_pL_q$ can be any suitable conjugate anion of an oxygen acid, as described herein, in any suitable oxidation state. Generally, X is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, and heteroaromatic borate. As used herein, carboxylates can be alkylated variants (e.g., acetate), fluorinated variants (e.g., trifluoroacetate (TFA)), or arylated variants (e.g., benzoates or benzoic acids). As used herein, "alkylated variants" and "arylated variants" refer to a carboxylic acid containing an alkyl group or an aryl group, respectively, as defined herein. Similarly, sulfonates can be alkylated variants (e.g., methanesulfonate) or fluorinated variants (e.g., trifluoromethanesulfonate). In certain embodiments, X is one or more selected from trifluoroacetate, acetate, benzoate, sulfate, methanesulfonate, and trifluoromethanesulfonate. Typically, X has an oxidation state of −4, −3, −2, or −1.

As used herein, "aliphatic" refers to a substituted or unsubstituted $C_1$-$C_9$ alkyl substituent, in which, "$C_1$-$C_9$ alkyl" refers to an alkyl carbon chain from 1 to 9 (i.e., 1, 2, 3, 4, 5, 6, 7, 8, or 9) carbons in length. In some embodiments, $C_1$-$C_9$ alkyl can be saturated, unsaturated, branched, straight-chained, cyclic, or a combination thereof. An exemplary, but non-limiting list of $C_1$-$C_9$ alkyl aliphatics includes methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, and a combination thereof. In certain embodiments, the aliphatic group is perfluorinated.

As used herein, "heteroaliphatic" refers to refers to a substituted or unsubstituted $C_1$-$C_9$ alkyl substituent which contains at least 1 heteroatom (e.g., O, S, N, and/or P) in the core of the molecule (i.e., the carbon backbone). The $C_1$-$C_9$ alkyl substituent can be saturated, unsaturated, branched, straight-chained, cyclic, or a combination thereof. In certain instances, the heteroaliphatic substituent has at least 2 heteroatoms in the core of the molecule (e.g., at least 3, 4, 5, or 6 heteroatoms in the core of the molecule). In some embodiments, the heteroaliphatic compound is an ether, an ester, a carbonate, an amide, an amine, a carbamate, a thioether, a thioester, a phosphate, a heterocycloalkane, or a combination thereof. In certain embodiments, the heteroaliphatic group is perfluorinated.

As used herein, the term "aromatic" group refers to an unsubstituted or substituted aromatic carbocyclic moiety that is planar and comprises 4n+2 π electrons, according to Hückel's Rule, wherein n=1, 2, or 3, as commonly understood in the art. The term "aromatic" includes monocyclic and polycyclic aromatics and generally contains from, for example, 6 to 30 carbon atoms (e.g., from 6 to 18 carbons, from 6 to 14 carbons, or from 6 to 10 carbons). An exemplary, but non-limiting list of aromatic substituents includes phenyl, xylenyl, naphthyl, biphenyl, anthracyl, or a combination thereof. In certain embodiments, the aromatic group is perfluorinated.

As used herein, "heteroaromatic" refers to a substituted or unsubstituted, monocyclic or polycylic aromatic compound which has at least one heteroatom (e.g., O, S, or N) in at least one of the rings. In certain embodiments, the heteroaromatic substituent is polycyclic and has 2, 3, or 4 aromatic rings. Each ring of the heteroaromatic substituent containing a heteroatom can contain one or two oxygen and/or sulfur atoms and/or from one to four nitrogen atoms, provided that the total number of heteroatoms in each ring is 4 or less and each ring has at least one carbon atom. The fused rings completing the polycyclic groups can contain only carbon atoms and can be saturated, partially saturated, or unsaturated. The nitrogen and sulfur atoms can optionally be oxidized, and the nitrogen atoms can optionally be quaternized. Heteroaromatic substituents that are polycyclic must include at least one fully aromatic ring but the other fused ring(s) can be aromatic or non-aromatic. In some embodiments, the heteroaromatic substituent is pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, pyridazinyl, or a combination thereof. In certain embodiments, the heteroaromatic group is perfluorinated.

As used herein, the term "substituted" can mean that one or more hydrogens on the designated atom or group are replaced with another group provided that the designated atom's normal valence is not exceeded. For example, when the substituent is oxo (i.e., =O), then two hydrogens bonded to the atom are replaced. In certain embodiments, the substituent is halo (e.g., fluoro, chloro, bromo, iodo), hydroxyl, cyano, nitro, alkoxy, amino, aryl, heteroaryl, alkyl, heteroalkyl, oxo, or combinations thereof. In certain embodiments, the substituent is fluoro. For example, the aliphatic, heteroaliphatic, aromatic, or heteroaromatic group can be fluorinated or perfluorinated. Combinations of substituents and/or variables are permissible provided that the substitutions do not significantly adversely affect synthesis or use of the compound. The substituted moiety typically comprises at least one substituent (e.g., 1, 2, 3, 4, 5, 6, etc.) in any suitable position (e.g., 1-, 2-, 3-, 4-, 5-, or 6-position, etc.).

The ligand (L) of the formula $M^{+n}X_pL_q$ can be any ligand that suitably coordinates to the main group element (M). Generally, each ligand is the same or different and each can be anionic or neutral. In some embodiments, each ligand (L) is independently an oxide (e.g., a bridging oxide (bridging oxo) or a terminal oxide (terminal oxo)), hydroxide, or combination thereof. In certain embodiments, the ligand is anionic and helps balance the charge of the oxidizing electrophile. In certain embodiments, the ligand is neutral and helps solvate the charge of the oxidizing electrophile. In some embodiments, the ligand is the non-oxidizable liquid, a substrate molecule, a product of the substrate oxidation, or a combination thereof.

In some embodiments, the ligand is at least one monodentate or bidentate ligand that is aliphatic-based or aromatic-based and comprises at least one oxo, thiol, sulfonyl, or carboxyl group, and optionally comprises one or more electron withdrawing groups (e.g., —NO$_2$, fluoro-C$_{1-8}$ alkyl, —F, —OOCR, —COOH, —OH$_2^+$, —CONH$_2$, —COOR, —NR$_3^+$, —CN, —SO$_3$H, —SO$_3$R, —SO$_3$W, or a combination thereof, in which R is hydrogen or any aliphatic (e.g., C$_{1-8}$ alkyl, fluoro-C$_{1-8}$ alkyl), heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal). In certain embodiments, the ligand comprises at least one carboxyl group. As used herein, "aliphatic-based" or "aromatic-based" refer to the ligand as a whole, and the ligand can be bound directly to the aliphatic or aromatic portion, or indirectly via at least one oxo, thiol, sulfonyl, or carboxyl group. The terms "aliphatic" and "aromatic" are as described herein.

In certain embodiments, the ligand is aromatic-based. Preferably, in embodiments where the ligand is aromatic-based, the ligand comprises at least one carboxyl group and/or at least one nitro group.

In certain embodiments, the ligand is selected from the group consisting of:

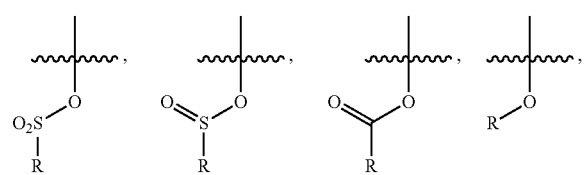

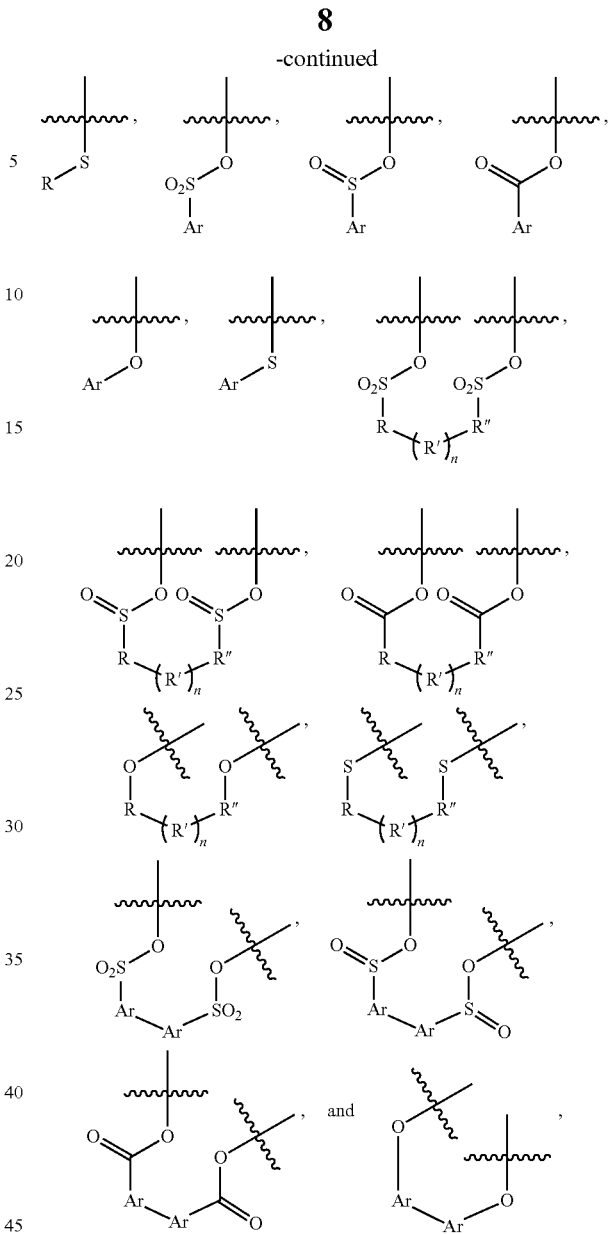

wherein R, R', and R" are the same or different and each is an optionally substituted alkyl, Ar is an optionally substituted aryl, and n is 0 or an integer of 1 to 6.

The ligand also can be of the formula —Ar-EWG, wherein Ar is an optionally substituted aryl and EWG is at least one electron withdrawing group, as described herein. For example, the electron withdrawing group can be at least one moiety selected from —NO$_2$, fluoro-C$_{1-8}$ alkyl, —F, —OOCR, —COOH, —OH$_2^+$, —CONH$_2$, —COOR, —NR$_3^+$, —CN, —SO$_3$H, —SO$_3$R, —SO$_3$W, and a combination thereof. In the context of the electron withdrawing group, R is hydrogen or any aliphatic (e.g., C$_{1-8}$ alkyl, fluoro-C$_{1-8}$ alkyl), heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal.

For example, the ligand can be:

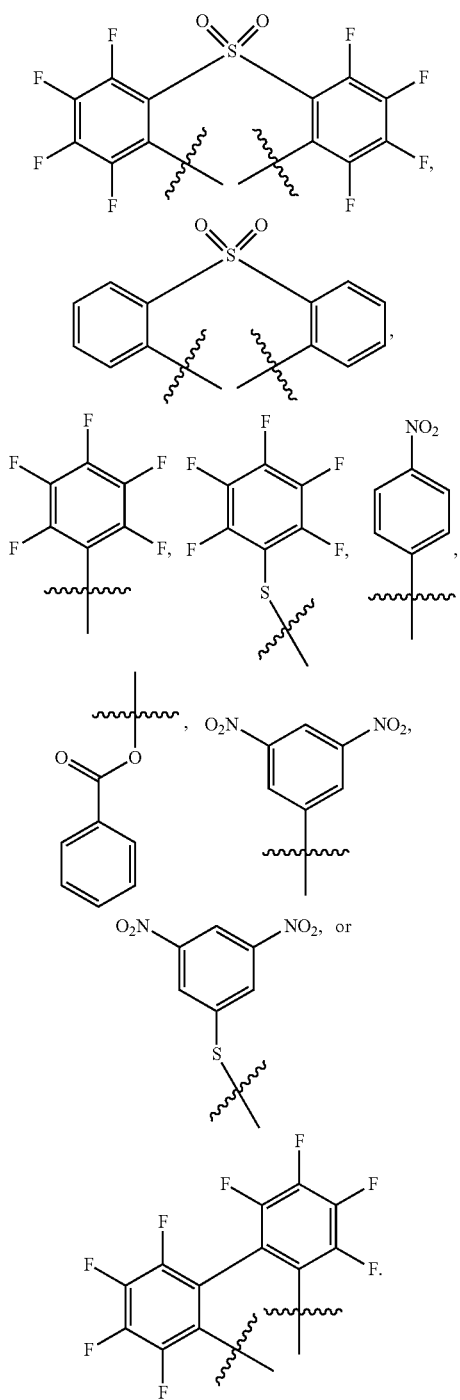

The ligand can be present in the mixture in less than stoichiometric quantities relative to the main group element, stoichiometric quantities relative to the main group element, or at least stoichiometric quantities relative to the main group element.

Figure 2:
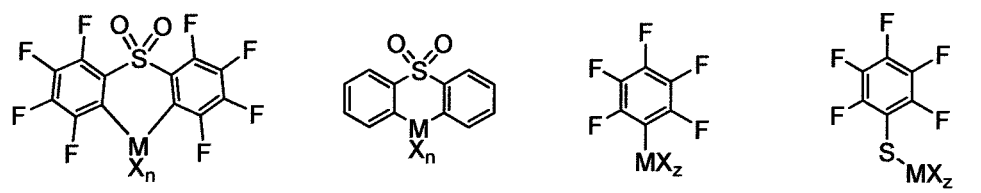
FIG. 2 is a list of exemplary oxidizing electrophiles.
Figure 2:
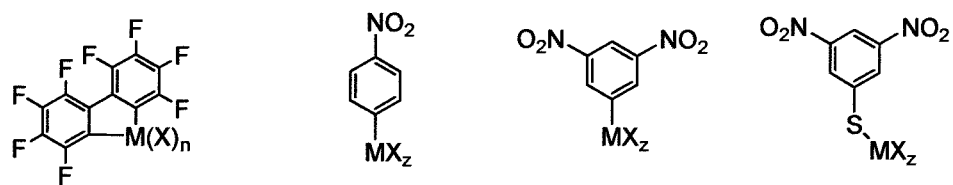

In some embodiments, the oxidizing electrophile has a formula according to any one of the structures in FIG. 2.

In certain embodiments of the present invention, the liquid medium and/or oxidizing composition comprises one or more additives. Depending on the embodiment, the additive can be a non-oxidizable liquid, a salt additive, a Lewis acid, or water. Desirably, the additives can be used to provide a functional benefit to the reaction mixture (e.g., liquid medium and/or composition), such as solvation, solubilization, viscosity modification, and/or charge transfer.

The amount of additive is not particularly limited such that the additive can be used in amounts that are a fraction of the amount of oxidizing electrophile or in amounts that are in large excess of the amount of oxidizing electrophile. The one or more additives can be present in a total amount of about 0.1 mol % of the oxidizing electrophile or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the one or more additives can be present in an amount of about 2000 mol % of the oxidizing electrophile or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or can be used alone to define an open-ended range. Thus, the one or more additives can be present in an amount between about 0 mol % to about 2000 mol % of the oxidizing electrophile, for example, about 0 mol % to about 1500 mol %, about 0 mol % to about 1000 mol %, about 0 mol % to about 900 mol %, about 0 mol % to about 800 mol %, about 0 mol % to about 700 mol %, about 0 mol % to about 600 mol %, about 0 mol % to about 500 mol %, about 0 mol % to about 400 mol %, about 0 mol % to about 300 mol %, about 0 mol % to about 200 mol %, about 0 mol % to about 100 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %. In some embodiments, the additive is not present (i.e., about 0 mol % or below the level of detection) in the liquid medium and/or oxidizing composition.

In some embodiments, the non-oxidizable liquid is selected from a fluorinated hydrocarbon, a sulfone, a deactivated arene, a deactivated aliphatic, a deactivated heteroarene, a deactivated heteroaliphatic, a carbonate, and a combination thereof.

In some embodiments, the non-oxidizable liquid is one or more suitable fluorinated hydrocarbon(s). The fluorinated hydrocarbon can be at least one fluorinated or perfluorinated straight chain aliphatic comprising at least 2 carbons, for example, at least 3, 4, 5, 6, 7, 8, 9, 10, 11, 12, 13, 14, 15, or 16 carbons. Preferably, the fluorinated hydrocarbon is at least one fluorinated or perfluorinated cyclic aliphatic comprising at least 3 carbons, for example, at least 4, 5, 6, 7, 8, 9, or 10 carbons. In some embodiments, the fluorinated or perfluorinated cyclic aliphatic can be monocyclic, bicyclic, or tricyclic. The fluorinated hydrocarbon can be perfluorinated and is branched or straight, and either substituted or unsubstituted. Preferably, the fluorinated or perfluorinated straight chain aliphatic and/or the fluorinated or perfluorinated cyclic aliphatic is substituted with one or more aliphatic substituents. More preferably, the fluorinated hydrocarbon is perfluorinated.

Specific examples include perfluropentane, perfluorohexane, perfluoroheptane, perfluorooctane, perfluorononane, perfluorodecane, perfluorocyclohexane, perfluorocycloheptane, perfluorocyclooctane, perfluorodecalin, perfluoromethylcyclohexane, perfluorodimethylcyclohexane, perfluorotrimethylcyclohexane, perfluoroethylcyclohexane, perfluorodiethylcyclohexane, perfluorotriethylcyclohexane, perfluoroethylmethylcyclohexane, and perfluoro-2,2,3,3-tetramethylbutane.

In some embodiments, the non-oxidizable liquid is one or more sulfone(s) of the formula:

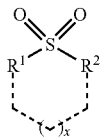

in which $R^1$ and $R^2$ are independently chosen from an aryl group and alkyl group, each of which is optionally substituted, the dashed lines represent optional bonds and atoms (e.g., C, N, O, S, or P), and x is an integer from 0 to 3 (i.e., 0, 1, 2, or 3). In certain embodiments, $R^1$ and $R^2$ are connected by a chain to produce a cyclic sulfone.

In some embodiments, the sulfone is at least one alkyl sulfone, in which both $R^1$ and $R^2$ are independently chosen as alkyl groups. The alkyl group can be any suitable straight chain, branched, or cyclic alkyl group (e.g., $C_{1-9}$ alkyl). In certain embodiments, the alkyl group is substituted with at least 1 electron withdrawing substituent (e.g., at least 2, 3, or 4 electron withdrawing substituents), such as those described herein. In certain embodiments, the alkyl groups are connected by an alkylene chain to produce a cyclic alkyl sulfone, such as sulfolane.

As used herein, "alkyl" refers to an aliphatic substituent that can be substituted, unsubstituted, branched, straight-chained, cyclic, or a combination thereof, and can be fully saturated or include portions that are unsaturated or aromatic. In some embodiments, the alkyl is $C_1$-$C_9$ alkyl, such as methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof.

In some embodiments, the alkyl is a heteroalkyl group, a cycloalkyl group, or a heterocycloalkyl group.

As used herein, "heteroalkyl" refers to a substituted or unsubstituted alkyl which contains at least 1 heteroatom (e.g., O, S, N, and/or P) in the core of the molecule (i.e., any part of the molecule except for the alkane-containing portion). Accordingly, at least 1 heteroatom can be a pendant substituent or part of a carbon chain. In certain instances, the heteroalkyl group has at least 2 heteroatoms in the core of the molecule (e.g., at least 3, 4, 5, or 6 heteroatoms in the core of the molecule). In some embodiments, the heteroalkyl group comprises a moiety selected from an ether, an ester, a carbonate, an amide, an amine, a carbamate, a thioether, a thioester, a phosphate, a heterocycloalkane, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof.

The term "cycloalkyl," as used herein, refers to a substituted or unsubstituted alkyl group comprising a cyclic alkane moiety containing from, for example, 3 to 6 carbon atoms or from 5 to 6 carbon atoms. In some embodiments, the cycloalkyl group is cyclopropyl, cyclobutyl, cyclopentyl, or cyclohexyl. In some embodiments, the cycloalkyl can be a cycloalkenyl, as long as the cycloalkenyl comprises an alkane-containing portion. The term "cycloalkenyl" refers to a cycloalkane, as described herein, with at least one C—C double bond in the ring. For example, the cycloalkenyl can be cyclopentenyl or cyclohexenyl.

The term "heterocycloalkyl," as used herein, refers to an alkyl group comprising a cyclic alkane moiety containing from, for example, 3 to 6 carbon atoms or from 5 to 6 carbon atoms which contains at least 1 heteroatom (e.g., O, S, N, and/or P) in the core of the molecule (i.e., any part of the molecule except for the alkane-containing portion). Accordingly, at least 1 heteroatom can be a pendant substituent or encompassed in a cyclic chain. In certain instances, the heterocycloalkyl has at least 2 heteroatoms in the core of the molecule (e.g., at least 3, 4, 5, or 6 heteroatoms in the core of the molecule). In some embodiments, the heterocycloalkyl group comprises a moiety selected from an ether, an ester, a carbonate, an amide, an amine, a carbamate, a thioether, a thioester, a phosphate, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof. An exemplary, but non-limiting list of heterocycloalkyl groups includes tetrahydrofuranyl, piperazinyl, morpholinyl, cyclohexanonyl, and 2-cyclohexylethanolyl.

As used herein, "aryl group" refers to any suitable substituted or unsubstituted aromatic or heteroaromatic group, as described herein. In some embodiments of the non-oxidizable liquid, the aryl group is deactivated, which means the aryl group is substituted with at least 1 electron withdrawing substituent, for example, at least 2, 3, or 4 electron withdrawing substituents, such as those described herein.

In some embodiments, the sulfone is a non-oxidizable liquid that contains a sulfonyl (—$SO_2$) functional group, such as (methylsulfonyl)benzene, (ethylsulfonyl)benzene, (propylsulfonyl)benzene, (isopropylsulfonyl)benzene, (butylsulfonyl)benzene, (methylsulfonyl)pyridine, (ethylsulfonyl)pyridine, (propylsulfonyl)pyridine, (isopropylsulfonyl) pyridine, (butylsulfonyl)pyridine, (cyclohexylsulfonyl) benzene, sulfonyldibenzene, dibenzothiophene 5,5-dioxide, 2,3-dihydrobenzothiophene 1,1-dioxide, or thiochromane 1,1-dioxide, each of which is substituted or unsubstituted.

In some embodiments, the sulfone is (methylsulfonyl) methane ("dimethyl sulfone"), (methylsulfonyl)ethane, tetrahydrothiophene 1,1-dioxide ("sulfolane"), tetrahydro-2H-thiopyran 1,1-dioxide, thietane 1,1-dioxide, (ethylsulfonyl) ethane, 1-(ethylsulfonyl)propane, 1-(propylsulfonyl) propane, 1-(propylsulfonyl)butane, 1-(butylsulfonyl)butane, 2-(ethylsulfonyl)propane, 2-(isopropylsulfonyl)propane, 1-(ethylsulfonyl)-2-methylpropane, 1-(methylsulfonyl)butane, 1-(ethylsulfonyl)butane, 1-(isopropylsulfonyl)-2-methylpropane, 1-(ethylsulfonyl)-2-methylpropane, 2-methyl-1-(methylsulfonyl)propane, 1-(isobutylsulfonyl)-2-methylpropane, 2-(tert-butylsulfonyl)-2-methylpropane, perfluorinated (methylsulfonyl)methane, perfluorinated (methylsulfonyl)ethane, perfluorinated tetrahydrothiophene 1,1-dioxide, perfluorinated tetrahydro-2H-thiopyran 1,1-dioxide, perfluorinated thietane 1,1-dioxide, perfluorinated (ethylsulfonyl)ethane, perfluorinated 1-(ethylsulfonyl)propane, perfluorinated 1-(propylsulfonyl)propane, perfluorinated 1-(propylsulfonyl)butane, perfluorinated 1-(butylsulfonyl)butane, perfluorinated 2-(ethylsulfonyl)propane, perfluorinated 2-(isopropylsulfonyl)propane, perfluorinated 1-(ethylsulfonyl)-2-methylpropane, perfluorinated 1-(methylsulfonyl)butane, perfluorinated 1-(ethylsulfonyl)butane, perfluorinated 1-(isopropylsulfonyl)-2-methylpropane, perfluorinated 1-(ethylsulfonyl)-2-methylpropane, perfluorinated 2-methyl-1-(methylsulfonyl)propane, perfluorinated 1-(isobutylsulfonyl)-2-methylpropane, or perfluorinated 2-(tert-butylsulfonyl)-2-methylpropane, each of which is substituted or unsubstituted.

In other embodiments, the sulfone is (methylsulfonyl)methane ("dimethyl sulfone"), (methylsulfonyl)ethane, tetrahydrothiophene 1,1-dioxide ("sulfolane"), tetrahydro-2H-thiopyran 1,1-dioxide, thietane 1,1-dioxide, perfluorinated (methylsulfonyl)methane, perfluorinated (methylsulfonyl)ethane, perfluorinated tetrahydrothiophene 1,1-dioxide, perfluorinated tetrahydro-2H-thiopyran 1,1-dioxide, or perfluorinated thietane 1,1-dioxide.

In some embodiments, the non-oxidizable liquid is one or more deactivated arene(s). As used herein, "deactivated arene" refers to at least one monocyclic or polycyclic aromatic compound that has 1 or more electron withdrawing substituents. In some embodiments, the arene compound has 2 or more electron withdrawing substituents, for example, 3 or more, 4 or more, 5 or more, or 6 or more electron withdrawing substituents. In some embodiments, each carbon of the deactivated arene has at least one electron withdrawing substituent. In certain embodiments, the deactivated arene is polycyclic and has 2, 3, or 4 aromatic rings and includes, e.g., benzene, toluene, xylene, naphthalene, biphenyl, and anthracene. The electron withdrawing substituent can be any suitable electron withdrawing substituent, such as those described herein.

An exemplary, but non-limiting list of deactivated arenes (e.g., deactivated benzenes) includes $C_6H_5(NO_2)$, $C_6H_5(CF_3)$, $C_6H_5F$, $C_6H_5(COOH)$, $C_6H_5(CONH_2)$, $C_6H_5(COOCF_3)$, $C_6H_5(OOCCF_3)$, $C_6H_5(CN)$, $C_6H_5(SO_3H)$, $C_6H_5(SO_3R)$, $C_6H_5(SO_3Q)$, m-$C_6H_4(NO_2)_2$, o-$C_6H_4(NO_2)_2$, p-$C_6H_4(NO_2)_2$, m-$C_6H_4(CF_3)_2$, o-$C_6H_4(CF_3)_2$, p-$C_6H_4(CF_3)_2$, m-$C_6H_4F_2$, o-$C_6H_4F_2$, p-$C_6H_4F_2$, m-$C_6H_4(COOH)_2$, o-$C_6H_4(COOH)_2$, p-$C_6H_4(COOH)_2$, m-$C_6H_4(CONH_2)_2$, o-$C_6H_4(CONH_2)_2$, p-$C_6H_4(CONH_2)_2$, m-$C_6H_4(COOCF_3)_2$, o-$C_6H_4(COOCF_3)_2$, p-$C_6H_4(COOCF_3)_2$, m-$C_6H_4(OOCCF_3)_2$, o-$C_6H_4(OOCCF_3)_2$, p-$C_6H_4(OOCCF_3)_2$, m-$C_6H_4(CN)_2$, o-$C_6H_4(CN)_2$, p-$C_6H_4(CN)_2$, m-$C_6H_4(SO_3H)_2$, o-$C_6H_4(SO_3H)_2$, p-$C_6H_4(SO_3H)_2$, m-$C_6H_4(SO_3R)_2$, o-$C_6H_4(SO_3R)_2$, p-$C_6H_4(SO_3R)_2$, m-$C_6H_4(SO_3Q)_2$, o-$C_6H_4(SO_3Q)_2$, p-$C_6H_4(SO_3Q)_2$, m-$C_6H_4(CF_3)(NO_2)$, o-$C_6H_4(CF_3)(NO_2)$, p-$C_6H_4(CF_3)(NO_2)$, m-$C_6H_4(CF_3)(F)$, o-$C_6H_4(CF_3)(F)$, p-$C_6H_4(CF_3)(F)$, m-$C_6H_4(CF_3)(COOH)$, o-$C_6H_4(CF_3)(COOH)$, p-$C_6H_4(CF_3)(COOH)$, m-$C_6H_4(CF_3)(CONH_2)$, o-$C_6H_4(CF_3)(CONH_2)$, p-$C_6H_4(CF_3)(CONH_2)$, m-$C_6H_4(CF_3)(CN)$, o-$C_6H_4(CF_3)(CN)$, p-$C_6H_4(CF_3)(CN)$, m-$C_6H_4(CF_3)(SO_3H)$, o-$C_6H_4(CF_3)(SO_3H)$, p-$C_6H_4(CF_3)(SO_3H)$, m-$C_6H_4(CF_3)(SO_3R)$, o-$C_6H_4(CF_3)(SO_3R)$, p-$C_6H_4(CF_3)(SO_3R)$, m-$C_6H_4(CF_3)(SO_3Q)$, o-$C_6H_4(CF_3)(SO_3Q)$, p-$C_6H_4(CF_3)(SO_3Q)$, m-$C_6H_4(F)(NO_2)$, o-$C_6H_4(F)(NO_2)$, p-$C_6H_4(F)(NO_2)$, m-$C_6H_4(COOH)(NO_2)$, o-$C_6H_4(COOH)(NO_2)$, p-$C_6H_4(COOH)(NO_2)$, m-$C_6H_4(CONH_2)(NO_2)$, o-$C_6H_4(CONH_2)(NO_2)$, p-$C_6H_4(CONH_2)(NO_2)$, m-$C_6H_4(COOCF_3)(NO_2)$, o-$C_6H_4(COOCF_3)(NO_2)$, p-$C_6H_4(COOCF_3)(NO_2)$, m-$C_6H_4(OOCCF_3)(NO_2)$, o-$C_6H_4(OOCCF_3)(NO_2)$, p-$C_6H_4(OOCCF_3)(NO_2)$, m-$C_6H_4(CN)(NO_2)$, o-$C_6H_4(CN)(NO_2)$, p-$C_6H_4(CN)(NO_2)$, m-$C_6H_4(SO_3H)(NO_2)$, o-$C_6H_4(SO_3H)(NO_2)$, p-$C_6H_4(SO_3H)(NO_2)$, m-$C_6H_4(SO_3R)(NO_2)$, o-$C_6H_4(SO_3R)(NO_2)$, p-$C_6H_4(SO_3R)(NO_2)$, m-$C_6H_4(SO_3Q)(NO_2)$, o-$C_6H_4(SO_3Q)(NO_2)$, p-$C_6H_4(SO_3Q)(NO_2)$, 1,2,3-$C_6H_3(CF_3)_2(NO_2)$, 1,3,4-$C_6H_3(CF_3)_2(NO_2)$, 1,3,5-$C_6H_3(CF_3)_2(NO_2)$, 1,2,3-$C_6H_3(CF_3)(NO_2)_2$, 1,3,4-$C_6H_3(CF_3)(NO_2)_2$, 1,3,5-$C_6H_3(CF_3)(NO_2)_2$, 1,2,3-$C_6H_3F_2(NO_2)$, 1,3,4-$C_6H_3F_2(NO_2)$, 1,3,5-$C_6H_3F_2(NO_2)$, 1,2,3-$C_6H_3(CF_3)F_2$, 1,3,4-$C_6H_3(CF_3)F_2$, 1,3,5-$C_6H_3(CF_3)F_2$, 1,2,3-$C_6H_3(COOH)_2(NO_2)$, 1,3,4-$C_6H_3(COOH)_2(NO_2)$, 1,3,5-$C_6H_3(COOH)_2(NO_2)$, 1,2,3-$C_6H_3(CF_3)(COOH)_2$, 1,3,4-$C_6H_3(CF_3)(COOH)_2$, 1,3,5-$C_6H_3(CF_3)(COOH)_2$, 1,2,3-$C_6H_3(CONH_2)_2(NO_2)$, 1,3,4-$C_6H_3(CONH_2)_2(NO_2)$, 1,3,5-$C_6H_3(CONH_2)_2(NO_2)$, 1,2,3-$C_6H_3(CF_3)(CONH_2)_2$, 1,3,4-$C_6H_3(CF_3)(CONH_2)_2$, 1,3,5-$C_6H_3(CF_3)(CONH_2)_2$, 1,2,3-$C_6H_3(COOCF_3)_2(NO_2)$, 1,3,4-$C_6H_3(COOCF_3)_2(NO_2)$, 1,3,5-$C_6H_3(COOCF_3)_2(NO_2)$, 1,2,3-$C_6H_3(CF_3)(COOCF_3)_2$, 1,3,4-$C_6H_3(CF_3)(COOCF_3)_2$, 1,3,5-$C_6H_3(CF_3)(COOCF_3)_2$, 1,2,3-$C_6H_3(OOCCF_3)_2(NO_2)$, 1,3,4-$C_6H_3(OOCCF_3)_2(NO_2)$, 1,3,5-$C_6H_3(OOCCF_3)_2(NO_2)$, 1,2,3-$C_6H_3(CF_3)(OOCCF_3)_2$, 1,3,4-$C_6H_3(CF_3)(OOCCF_3)_2$, 1,3,5-$C_6H_3(CF_3)(OOCCF_3)_2$, 1,2,3-$C_6H_3(CN)_2(NO_2)$, 1,3,4-$C_6H_3(CN)_2(NO_2)$, 1,3,5-$C_6H_3(CN)_2(NO_2)$, 1,2,3-$C_6H_3(SO_3H)(CN)_2$, 1,3,4-$C_6H_3(SO_3H)(CN)_2$, 1,3,5-$C_6H_3(SO_3H)(CN)_2$, 1,2,3-$C_6H_3(SO_3R)(CN)_2$, 1,3,4-$C_6H_3(SO_3R)(CN)_2$, 1,3,5-$C_6H_3(SO_3R)(CN)_2$, 1,2,3-$C_6H_3(SO_3Q)(CN)_2$, 1,3,4-$C_6H_3(SO_3Q)(CN)_2$, 1,3,5-$C_6H_3(SO_3Q)(CN)_2$, 1,2,3-$C_6H_3(CF_3)_2(SO_3H)$, 1,3,4-$C_6H_3(CF_3)_2(SO_3H)$, 1,3,5-$C_6H_3(CF_3)_2(SO_3H)$, 1,2,3-$C_6H_3(CF_3)_2(SO_3R)$, 1,3,4-$C_6H_3(CF_3)_2(SO_3R)$, 1,3,5-$C_6H_3(CF_3)_2(SO_3R)$, 1,2,3-$C_6H_3(CF_3)_2(SO_3Q)$, 1,3,4-$C_6H_3(CF_3)_2(SO_3Q)$, 1,3,5-$C_6H_3(CF_3)_2(SO_3Q)$, 1,2,3-$C_6H_3(CF_3)_3$, 1,3,4-$C_6H_3(CF_3)_3$, 1,3,5-$C_6H_3(CF_3)_3$, 1,2,3-$C_6H_3(NO_2)_3$, 1,3,4-$C_6H_3(NO_2)_3$, 1,3,5-$C_6H_3(NO_2)_3$, 1,2,3-$C_6H_3F_3$, 1,3,4-$C_6H_3F_3$, 1,3,5-$C_6H_3F_3$, 1,2,3-$C_6H_3(COOH)_3$, 1,3,4-$C_6H_3(COOH)_3$, 1,3,5-$C_6H_3(COOH)_3$, 1,2,3-$C_6H_3(COOCF_3)_3$, 1,3,4-$C_6H_3(COOCF_3)_3$, 1,3,5-$C_6H_3(COOCF_3)_3$, 1,2,3-$C_6H_3(OOCCF_3)_3$, 1,3,4-$C_6H_3(OOCCF_3)_3$, 1,3,5-$C_6H_3(OOCCF_3)_3$, 1,2,3-$C_6H_3(CN)_3$, 1,3,4-$C_6H_3(CN)_3$, 1,3,5-$C_6H_3(CN)_3$, 1,2,3-$C_6H_3(SO_3H)_3$, 1,3,4-$C_6H_3(SO_3H)_3$, 1,3,5-$C_6H_3(SO_3H)_3$, 1,2,3-$C_6H_3(SO_3R)_3$, 1,3,4-$C_6H_3(SO_3R)_3$, 1,3,5-$C_6H_3(SO_3R)_3$, 1,2,3-$C_6H_3(SO_3Q)_3$, 1,3,4-$C_6H_3(SO_3Q)_3$, 1,3,5-$C_6H_3(SO_3Q)_3$, 1,2,3-$C_6H_3(CONH_2)_3$, 1,3,4-$C_6H_3(CONH_2)_3$, and 1,3,5-$C_6H_3(CONH_2)_3$. As used herein, R is any aliphatic (e.g., $C_{1-8}$ alkyl, fluoro-$C_{1-8}$ alkyl), heteroaliphatic, aromatic, or heteroaromatic moiety, each of which is optionally substituted, and Q refers to a cation.

In certain embodiments, the non-oxidizable liquid is a nitroarene. As used herein, "nitroarene" refers to any deactivated arene comprising at least one nitro group. For example, the nitroarene can be nitro-substituted benzene, nitro-substituted toluene, nitro-substituted xylene, nitro-substituted naphthalene, nitro-substituted biphenyl, or nitro-substituted anthracene.

In some embodiments, the non-oxidizable liquid is one or more deactivated aliphatic(s). As used herein, "deactivated aliphatic" refers to at least one aliphatic group, as described herein, that has 1 or more electron withdrawing substituents (e.g., 2 or more, 3 or more, 4 or more, or 5 or more electron withdrawing substituents).

In some embodiments, the deactivated aliphatic non-oxidizable liquid is at least one saturated, unsaturated, branched, straight-chained, or cyclic $C_1$-$C_9$ alkyl aliphatic group that is substituted with at least 1 electron withdrawing substituent (e.g., 2 or more, 3 or more, 4 or more, or 5 or more electron withdrawing substituents). An exemplary, but non-limiting list of deactivated $C_1$-$C_9$ alkyl aliphatics is methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof, in which the $C_1$-$C_9$ alkyl is substituted with 1 or more electron withdrawing substituents.

In some instances, the deactivated aliphatic is methyl, ethyl, n-propyl, iso-propyl, n-butyl, sec-butyl, tent-butyl, n-pentyl, sec-pentyl, or neo-pentyl, in which the methyl, ethyl, n-propyl, iso-propyl, n-butyl, sec-butyl, tert-butyl, n-pentyl, sec-pentyl, or neo-pentyl is substituted with 1 or more electron withdrawing substituents. In certain embodiments, the deactivated aliphatic is methyl, ethyl, n-propyl, or iso-propyl in which the methyl, ethyl, n-propane, or iso-propyl is substituted with 1 or more electron withdrawing substituents.

In other embodiments, the deactivated aliphatic is trifluoromethanol, trifluoromethyl 2,2,2-trifluoroacetate, 2,2,2-trifluoroethan-1-ol, 2,2,2-trifluoroethyl 2,2,2-trifluoroacetate, perfluoroethyl 2,2,2-trifluoroacetate, 1,1,2,2,2-pentafluoroethan-1-ol, nitromethane, trifluoro(nitro)methane, 1,1,2,2-tetrafluoroethane-1,2-diol, 1,1,2,2-tetrafluoro-2-hydroxyethyl 2,2,2-trifluoroacetate, perfluoroethane-1,2-diyl bis(2,2,2-trifluoroacetate), ethane-1,2-diyl bis(2,2,2-trifluoroacetate), 1,1,2,2,3,3-hexafluoropropane-1,3-diol, propane-1,2,3-triyl tris(2,2,2-trifluoroacetate), oxalic acid, 1,1,1,4,4,4-hexafluorobutane-2,3-dione, methyl 2,2,2-trifluoroacetate, methyl 2,2,3,3,3-pentafluoropropanoate, or trifluoromethyl 2,2,3,3,3-pentafluoropropanoate.

In other embodiments, the deactivated aliphatic is trifluoromethyl acetate, 1,1-difluoroethyl acetate, 2,2,2-trifluoroethyl acetate, perfluoroethyl acetate, perfluoropropan-2-yl acetate, 1,1,1,3,3,3-hexafluoropropan-2-yl acetate, 1,1,2,2-tetrafluoro-2-hydroxyethyl acetate, perfluoroethane-1,2-diyl diacetate, ethane-1,2-diyl diacetate, propane-1,2,3-triyl trisacetate, perfluoropropane-1,2,3-triyl triacetate, 1,1,3,3-tetrafluoropropane-1,2,3-triyl triacetate, or 1,1-difluoroethane-1,2-diyl diacetate.

In some embodiments, the non-oxidizable liquid is one or more deactivated heteroarene(s). As used herein, "deactivated heteroarene" refers to at least one monocyclic or polycyclic heteroaromatic compound which has at least one heteroatom (O, S, or N) in at least one of the rings. The term "heteroaromatic" is as described herein.

In some embodiments, the deactivated heteroarene is isoxazole, oxazole, isothiazole, thiazole, imidazole, thiadiazole, tetrazole, triazole, oxadiazole, pyrazole, pyrazine, pyrimadine, or triazine, each of which is substituted or unsubstituted. In other preferred embodiments, the deactivated heteroarene is pyrrole, furan, thiophene, or pyridine, each of which is substituted with at least one substituent that is an electron withdrawing substituent.

In other embodiments, the deactivated heteroarene is perfluoroisoxazole, perfluorooxazole, perfluoroisothiazole, perfluorothiazole, perfluoroimidazole, perfluorothiadiazole, perfluorotetrazole, perfluorotriazole, perfluorooxadiazole, perfluoropyrazole, perfluoropyrazine, perfluorotriazine, perfluoropyrrole, perfluorofuran, perfluorothiophene, perfluoropyridine, nitropyrrole, nitrofuran, nitrothiophene, nitropyridine, cyanopyrrole, cyanofuran, cyanothiophene, cyanopyridine, picolinic acid, nicotinic acid, isonicotinic acid, pyridine sulfonic acid, pyrrole sulfonic acid, furan sulfonic acid, thiophene sulfonic acid, pyridine carboxylic acid, pyrrole carboxylic acid, furan carboxylic acid, thiophene carboxylic acid, trifluoromethyl pyridine, trifluoromethyl pyrrole, trifluoromethyl furan, or trifluoromethyl thiophene.

In some embodiments, the non-oxidizable liquid is one or more deactivated heteroaliphatic(s). The term "heteroaliphatic" is as described herein. In some embodiments, the heteroaliphatic compound is an ether, an ester, a carbonate, an amide, an amine, a carbamate, a thioether, a thioester, a phosphate, or a heterocycloalkane. The term "heterocycloalkane" refers to a cycloalkane, as described herein, in which at least one heteroatom (e.g., O, S, N, and/or P) replaces at least one carbon in the ring system. In an aspect, a heterocycloalkane is a 5-, 6-, or 7-membered monocyclic ring and contains one, two, or three heteroatoms selected from nitrogen, oxygen, and sulfur. Examples of such heterocycloalkane rings are pyrrolidine, pyrroline, pyran, piperidine, quinuclidine, imidazoline, dioxane, dioxolane, morpholine, thiomorpholine, trithiane, dithiane, pyrazoline, pyrazolidine, piperazine, or a combination thereof.

In certain embodiments, the deactivated heteroaliphatic has at least 1 electron withdrawing substituent. In some embodiments, the deactivated heteroaliphatic has at least 2 electron withdrawing substituents (e.g., at least 3, 4, 5, or 6 electron withdrawing substituents), such as those described herein.

For example, the deactivated heteroaliphatic compound can be trifluoro(trifluoromethoxy)methane, 1,1,1,2,2-pentafluoro-2-(trifluoromethoxy)ethane, 1,1,1,2,2-pentafluoro-2-(perfluoroethoxy)ethane, tris(trifluoromethyl)amine, 1,1,2,2,2-pentafluoro-N-(perfluoroethyl)-N-(trifluoromethyl) ethan-1-amine, tris(perfluoroethyl)amine, 2,2,2-trifluoro-N,N-bis(trifluoromethyl)acetamide, N,N-bis(trifluoromethyl) formamide, 2,2,2-trifluoroacetamide, perfluoropyrrolidine, perfluoropyrroline, perfluoropyran, perfluoropiperidine, perfluorodioxane, perfluoromorpholine, perfluoropiperazine, nitropyrrolidine, nitropyrroline, nitropyran, nitropiperidine, nitrodioxane, nitromorpholine, nitropiperazine, cyanopyrrolidine, cyanopyrroline, cyanopyran, cyanopiperidine, cyanodioxane, cyanomorpholine, cyanopiperazine, pyrrolidine carboxylic acid, pyrroline carboxylic acid, pyran carboxylic acid, piperidine carboxylic acid, dioxane carboxylic acid, morpholine carboxylic acid, piperazine carboxylic acid, pyrrolidine sulfonic acid, pyrroline sulfonic acid, pyran sulfonic acid, piperidine sulfonic acid, dioxane sulfonic acid, morpholine sulfonic acid, or piperazine sulfonic acid.

In some embodiments, the non-oxidizable liquid is one or more carbonate(s). The carbonate can be a chemical compound comprising at least one carbonate moiety (e.g., 1 carbonate, 2 carbonates, 3 carbonates, or 4 carbonates). For example, the carbonate can be an alkyl carbonate, a heteroalkyl carbonate, a cycloalkyl carbonate, a heterocycloalkyl carbonate, an aryl carbonate, hydrogen carbonate, or a combination thereof.

In any of the embodiments described herein, the electron withdrawing substituent can be any suitable electron withdrawing group, such as —$NO_2$, fluoro-$C_{1-8}$ alkyl, —F, —OOCR, —COOH, —$OH_2^+$, —$CONH_2$, —COOR, —$NR_3^+$, —CN, —$SO_3H$, —$SO_3R$, —$SO_3W$, or a combination thereof, in which R is hydrogen or any aliphatic (e.g., $C_{1-8}$ alkyl, fluoro-$C_{1-8}$ alkyl), heteroaliphatic, aromatic, or heteroaromatic, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal. In certain embodiments, R is —$CF_3$.

In some embodiments, the non-oxidizable liquid is the same as a product of the reaction described herein. For example, the non-oxidizable liquid can be the oxidized substrate (e.g., a product of the oxidation of propane can be 1,2-propane(trifluoroacetate), which is a deactivated heteroaliphatic).

In some embodiments, the liquid medium and/or oxidizing composition comprises a salt additive.

Generally, the salt additive is one or more compounds of the formula $Q_aZ_b$, in which Q is a cation, Z is a bridging oxide, a terminal oxide, a hydroxide, or an anion of the oxygen acid, a is an integer from 1 to 5 (i.e., 1, 2, 3, 4, or 5), b is an integer from 1 to 5 (i.e., 1, 2, 3, 4, or 5), and wherein a and b are the same or different and balance the oxidation states of Q and Z.

Q can be any suitable cation in any suitable oxidation state. In some embodiments, Q can be a proton, ammonium, a cation of an alkali metal, a cation of an alkaline earth metal, a cation of a rare-earth metal, a main group element cation, or a combination thereof. In some embodiments, Q is hydrogen or a cation of lithium, sodium, potassium, rubidium, cesium, francium, beryllium, magnesium, calcium, strontium, barium, or radium. Typically, Q has an oxidation state of +5, +4, +3, +2, or +1.

Z can be any suitable oxide (e.g., a bridging oxide or a terminal oxide), hydroxide, or anion of an oxygen acid, as described herein, in any suitable oxidation state. In some embodiments, Z is an anion of the oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, and heteroaromatic borate. In certain embodiments, Z is selected from a bridging oxide, a terminal oxide, hydroxide, sulfite, sulfate, hydrogen sulfate, thiosulfate, nitrite, nitrate, phosphite, phosphate, hydrogen phosphate, dihydrogen phosphate, carbonate, hydrogen carbonate, oxalate, cyanate, isocyanate, thiocyanate, carboxylate, sulfonate, and a combination thereof. As used herein, carboxylates can be alkylated variants (e.g., acetate), fluorinated variants (e.g., trifluoroacetate), or arylated variants (e.g., benzoates or benzoic acids). As used herein, "alkylated variants" and "arylated variants" refer to a carboxylic acid containing an alkyl group or an aryl group, respectively, as defined herein. Similarly, sulfonates can be alkylated variants (e.g., methanesulfonate) or fluorinated variants (e.g., trifluoromethanesulfonate). In certain embodiments, Z is one or more selected from trifluoroacetate, acetate, benzoate, sulfate, methanesulfonate, and trifluoromethanesulfonate. Typically, Z has an oxidation state of −4, −3, −2, or −1.

In preferred embodiments, the liquid medium and/or oxidizing composition comprises a salt of the oxygen acid.

In certain embodiments, X of the oxidizing electrophile formula $M^{+n}X_pL_q$ and Z of the additive are the same.

In certain embodiments, X of the oxidizing electrophile formula $M^{+n}X_pL_q$ and Z of the additive are different.

In some embodiments, $Q_aZ_b$ is a Brϕsted acid, a salt, or a combination thereof. In some instances, $Q_aZ_b$ is one or more of acetic acid, ammonium acetate, lithium acetate, sodium acetate, potassium acetate, rubidium acetate, cesium acetate, francium acetate, beryllium acetate, magnesium acetate, calcium acetate, strontium acetate, barium acetate, radium acetate, benzoic acid, ammonium benzoate, lithium benzoate, sodium, potassium benzoate, rubidium benzoate, cesium benzoate, francium benzoate, beryllium benzoate, magnesium benzoate, calcium benzoate, strontium benzoate, barium benzoate, radium benzoate, trifluoroacetic acid, ammonium trifluoroacetate, lithium trifluoroacetate, sodium trifluoroacetate, potassium trifluoroacetate, trifluoroacetic acid, ammonium trifluoroacetate, lithium trifluoroacetate, sodium trifluoroacetate, potassium trifluoroacetate, rubidium trifluoroacetate, cesium trifluoroacetate, francium trifluoroacetate, beryllium trifluoroacetate, magnesium trifluoroacetate, calcium trifluoroacetate, strontium trifluoroacetate, barium trifluoroacetate, radium trifluoroacetate, sulfuric acid, ammonium sulfate, lithium sulfate, sodium sulfate, potassium sulfate, rubidium sulfate, cesium sulfate, francium sulfate, beryllium sulfate, magnesium sulfate, calcium sulfate, strontium sulfate, barium sulfate, radium sulfate, phosphoric acid, methanesulfonic acid, ammonium methanesulfonate, lithium methanesulfonate, sodium methanesulfonate, potassium methanesulfonate, rubidium methanesulfonate, cesium methanesulfonate, francium methanesulfonate, beryllium methanesulfonate, magnesium methanesulfonate, calcium methanesulfonate, strontium methanesulfonate, barium methanesulfonate, radium methanesulfonate, trifluoromethanesulfonic acid, ammonium trifluoromethanesulfonate, lithium trifluoromethanesulfonate, sodium trifluoromethanesulfonate, potassium trifluoromethanesulfonate, rubidium trifluoromethanesulfonate, cesium trifluoromethanesulfonate, francium trifluoromethanesulfonate, beryllium trifluoromethanesulfonate, magnesium trifluoromethanesulfonate, calcium trifluoromethanesulfonate, strontium trifluoromethanesulfonate, barium trifluoromethanesulfonate, or radium trifluoromethanesulfonate. In preferred embodiments, $Q_aZ_b$ is trifluoroacetic acid, acetic acid, benzoic acid, methanesulfonic acid, or a combination thereof, each of which can be substituted or unsubstituted.

In some embodiments, the liquid medium and/or oxidizing composition comprises a Lewis Acid. Generally, the Lewis acid is of formula $Q_aZ_b$, wherein $Q_aZ_b$ is any suitable, non-halide containing Lewis acid, which is a strong electron pair acceptor. In embodiments where $Q_aZ_b$ is a non-halide containing Lewis acid, Q can be a cation of a transition metal, a cation of a rare-earth metal, a main group cation, or a combination thereof. In some embodiments, Q is a cation of boron, bismuth, antimony, arsenic, lanthanum, cerium, scandium, yttrium, titanium, zirconium, hafnium, silver, zinc, cadmium, aluminum, gallium, indium, germanium, tin, phosphorus, or a combination thereof. Typically, Q has an oxidation state of +5, +4, +3, +2, or +1. In certain embodiments, Q is In(III), Sc(III), Zn(II), Ti(IV), Al(III), Ga(III), B(III), Sb(III), Bi(III), or As(III). It will be understood that any one or more Q(s) can be combined with any one or more Z(s), such that fundamental chemical rules are satisfied, to form the non-halide containing Lewis acid (e.g., $Ce(OAc)_3$, $Ce(OTf)_2$, $Zn(OAc)_2$, $Zn(OTf)_2$, ZnO, $In(OAc)_3$, $In(OTf)_3$, $In_2O_3$, $Sb(OAc)_3$, $Sb(OTf)_3$, $Sb_2O_3$, $Bi(OAc)_3$, $Bi(OTf)_3$, $Bi_2O_3$, $Al(OTf)_3$, $Ga(OTf)_3$, $Sc(OAc)_3$, $Sc(OTf)_3$, or $Sc(OMs)_3$). As used herein, "OTf" refers to trifluoromethanesulfonate, "OMs" refers to mesylate, and "OAc" refers to acetate.

In some embodiments, the liquid medium and/or oxidizing composition does not contain a halide ion (e.g., $Cl^-$, $Br^-$, or $I^-$). As used herein, the term "halide ion" is considered different from the term halogen atom. In particular, the term halide ion does not encompass a halogen atom (e.g., a fluorine atom, a chlorine atom, a bromine atom, or an iodine atom) attached to an aliphatic or aromatic substituent (i.e., a substituent that will not decompose to form free ions under reaction conditions). For example, iodine can be present in aromatic-iodine species, as this form of iodine would not be considered a halide ion. Instead, the term "halide ion" refers to ions of salt additives, such as alkali halide compounds (e.g., NaI, KCl, etc.). Accordingly, the halide ion can be present in the liquid medium and/or oxidizing composition in an amount less than 0.1 mol % (e.g., less than 0.05 mol %, less than 0.01 mol %, less than 0.005 mol %, less than 0.001 mol %) or about 0 mol % of the main group element.

In some embodiments, the liquid medium and/or oxidizing composition comprises a trace amount of a halide ion (e.g., Cl⁻, Br⁻, or I⁻). It is possible that impurities in starting materials or from reactor corrosion can be responsible for the presence of trace halide ions. Accordingly, the halide ion can be present in an amount of about 0.00001 mol % of the main group element or more (e.g., about 0.0001 mol % or more, about 0.001 mol % or more, 0.01 mol % or more, 0.1 mol % or more, or about 1 mol % or more). Alternatively, or in addition, the halide ion can be present in an amount of about 5 mol % of the main group element or less (e.g., about 4 mol % or less, about 3 mol % or less, about 2 mol % or less, about 1 mol % or less, or about 0.1 mol % or less). Any two of the foregoing endpoints can be used to define a close-ended range, or any single endpoint can be used alone to define an open-ended range.

In some embodiments, the additive is water.

When the oxidizing composition consists essentially of (a) an oxidizing electrophile comprising a main group element in oxidized form and at least one conjugate anion of an oxygen acid; (b) a non-oxidizable liquid selected from a fluorinated hydrocarbon, a sulfone, a deactivated arene, a deactivated aliphatic, a deactivated heteroarene, a deactivated heteroaliphatic, and a combination thereof; and (c) optionally one or more salt additives of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z, compounds that exert a material effect (e.g., a superacid and/or a compound comprising at least one labile halide (e.g., F, Cl, Br, and/or I), such as halogen-based Lewis acids) on a substrate are excluded from the oxidizing composition. When the oxidizing composition consists of (a) an oxidizing electrophile comprising a main group element in oxidized form and at least one conjugate anion of an oxygen acid; (b) a non-oxidizable liquid selected from a fluorinated hydrocarbon, a sulfone, a deactivated arene, a deactivated aliphatic, a deactivated heteroarene, a deactivated heteroaliphatic, and a combination thereof; and (c) optionally one or more salt additives of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z, the composition excludes any other compounds. In an embodiment, the oxidizing composition is free of a compound that exerts a material effect that is a superacid and/or a compound comprising at least one labile halide.

The oxygen acid in the context of the oxidizing electrophile and the oxygen acid in the context of the additive are each independently chosen. Accordingly, the oxygen acid in the context of the oxidizing electrophile and the oxygen acid in the context of the additive can be the same or different. Typically, the oxygen acid in the context of the oxidizing electrophile and the oxygen acid in the context of the additive are the same.

The invention also provides a process for oxidizing a substrate. The process comprises (a) contacting a substrate and (i) an oxidizing electrophile comprising a main group element in oxidized form, or (ii) an oxidant and a reduced form of the oxidizing electrophile, in a liquid medium comprising a non-oxidizable liquid and optionally one or more additives selected from an oxygen acid, a salt additive, a Lewis acid, and water, to provide an oxidized substrate and a reduced form of the oxidizing electrophile; and (b) optionally separating the oxidized substrate and the reduced form of the oxidizing electrophile.

The process comprises contacting the substrate with an oxidizing electrophile comprising a main group element in oxidized form. The main group element in oxidized form can be any suitable main group element in any suitable oxidation state, as described herein. For example, the main group element can have an oxidation state of +7, +6, +5, +4, +3, +2, or +1, particularly an oxidation state of +6, +5, +4, +3, or +2. In preferred embodiments, the main group element in oxidized form has any oxidation state suitable for a one- or two-electron reduction/oxidation process.

In some embodiments, the process comprises contacting the substrate with an oxidant and a reduced form of an oxidizing electrophile. As used herein, "a reduced form of the oxidizing electrophile" refers to any reduced form of an oxidizing electrophile comprising a main group element. Generally, the reduced form of the oxidizing electrophile comprises a main group element with a one- or two-electron difference in oxidation state, relative to the oxidizing electrophile comprising a main group element in oxidized form. For example, the reduced form of the oxidizing electrophile will have a main group element in an oxidation state of +6, +5, +4, +3, +2, or +1, or a neutral oxidation state. In certain embodiments, the reduced form of the oxidizing electrophile comprises the main group element in an oxidation state of +4, +3, +2, or +1, or a neutral oxidation state. In some embodiments, the reduced form of the oxidizing electrophile can be any suitable chemical variant of the oxidizing electrophile, such that the main group element has been reduced by one or two electrons, preferably two electrons.

In certain embodiments, the reduced form of the oxidizing electrophile is of the formula $M^{+n-2}X_{p-2}L_q$, wherein M is a main group element cation in an oxidation state of n, X is the conjugate anion of an oxygen acid, L is a ligand, n and p are the same or different and each is an integer from 2 to 6 (i.e., 2, 3, 4, 5, or 6), and q is an integer from 0 to 6 (i.e., 0, 1, 2, 3, 4, 5, or 6). In certain embodiments, the reduced form of the oxidizing electrophile is of the formula $M^{+n-1}X_{p-1}L_q$, wherein M is a main group element cation in an oxidation state of n, X is the conjugate anion of an oxygen acid, L is a ligand, n is an integer from 2 to 6 (i.e., 2, 3, 4, 5, or 6), p is an integer from 1 to 6 (i.e., 1, 2, 3, 4, 5, or 6), and q is an integer from 0 to 6 (i.e., 0, 1, 2, 3, 4, 5, or 6). In certain embodiments, n and p are the same or different and each is an integer from 2 to 6 (i.e., 2, 3, 4, 5, 6), and q is an integer from 0 to 4 (i.e., 0, 1, 2, 3, or 4).

In some embodiments, the oxidizing electrophile used in the process has the formula $M^{+n}X_pL_q$, which undergoes reaction with the substrate in the liquid medium to yield a reduced form of the oxidizing electrophile of formula $M^{+(n-2)}X_{p-2}L_q$ or $M^{+(n-1)}X_{p-1}L_q$.

In embodiments where the process comprises contacting the substrate with an oxidant and a reduced form of an oxidizing electrophile, the oxidant can be any suitable oxidant capable of generating the main group element in oxidized form. For example, the oxidant (e.g., the oxidizing regeneration reagent) can be molecular oxygen, air, a peroxide, nitric oxide, nitrous oxide, nitric acid, sulfur trioxide, ozone, or a combination thereof. The oxidant can be used under an inert atmosphere, or in combination with air. The peroxide can be, e.g., an organic peroxide, inorganic peroxide, hydrogen peroxide, or a combination thereof. In some embodiments, the oxidant can be an organic oxidant. For example, the oxidant can be a quinone or a nitroxide. In certain embodiments, the oxidant is a quinone, molecular oxygen, air, a peroxide, nitric oxide, nitrous oxide, nitric acid, a nitroxide, sulfur trioxide, ozone, or a combination thereof.

The oxidizing electrophile can be prepared using any suitable method. For example, the oxidizing electrophile can be prepared separately as a stable and isolable compound or the oxidizing electrophile can be generated in situ from a reduced form of the oxidizing electrophile, generated in situ through a substitution reaction, or generated in situ through a dehydration reaction. A combination of any of these methods can also be used.

In some embodiments, the oxidizing electrophile comprising a main group element is present in at least stoichiometric quantities relative to the amount of oxidized substrate produced (i.e., relative to the amount of substrate that reacts with the oxidizing electrophile). Typically, when the oxidizing electrophile is present in at least a stoichiometric quantity relative to the oxidized substrate, an oxidizing regeneration reagent is not present in the reaction. In other embodiments, the oxidizing electrophile is present in a sub-stoichiometric quantity relative to the oxidized substrate. Typically, when the oxidizing electrophile is present in a sub-stoichiometric quantity, an oxidizing regeneration reagent and optionally an oxidative regeneration catalyst are present to regenerate the oxidizing electrophile from the reduced form of the oxidizing electrophile. In some preferred embodiments, the oxidizing electrophile is present in at least a stoichiometric quantity relative to the oxidized substrate and an oxidizing regeneration reagent and optionally an oxidative regeneration catalyst are not required, but can be present in the liquid medium. In other preferred embodiments, the oxidizing electrophile is present in a sub-stoichiometric quantity relative to the oxidized substrate and an oxidizing regeneration reagent or an oxidative regeneration catalyst are present. In some embodiments, the oxidizing electrophile comprising a main group element in oxidized form is present in less than stoichiometric quantities relative to the oxidized substrate and acts as a catalyst.

In some embodiments, the reduced form of the oxidizing electrophile can be present in at least stoichiometric quantities or a sub-stoichiometric quantity relative to the oxidized substrate (i.e., relative to the amount of substrate that reacts with the oxidizing electrophile). In some embodiments, the reduced form of the oxidizing electrophile is generated in situ from the reduction of the oxidizing electrophile upon formation of the oxidized substrate. In these instances, the reduced form of the oxidizing electrophile is used to regenerate the oxidizing electrophile. In other embodiments, the reduced form of the oxidizing electrophile is provided directly to the process for converting a substrate to an oxidized substrate. In these instances, the reduced form of the oxidizing electrophile is used to generate the oxidizing electrophile. Accordingly, when the reduced form of the oxidizing electrophile is provided directly to the process in at least stoichiometric quantities or sub-stoichiometric quantities, the oxidant is present in the reaction mixture to generate the oxidizing electrophile.

Thus, the process for oxidizing a substrate can comprise the oxidizing electrophile, the reduced form of the oxidizing electrophile, or both the oxidizing electrophile and the reduced form of the oxidizing electrophile. The amount of the oxidizing electrophile and/or the reduced form of the oxidizing electrophile is not particularly limited such that a sufficient amount of the oxidizing electrophile exists to oxidize the substrate. Accordingly, the oxidizing electrophile and/or the reduced form of the oxidizing electrophile can be present in an amount of about 0.1 mol % of the substrate or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxidizing electrophile and/or the reduced form of the oxidizing electrophile can be present in an amount of about 2000 mol % of the substrate or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used alone to define an open-ended range. For example, the oxidizing electrophile and/or the reduced form of the oxidizing electrophile can be present in an amount between about 0.1 mol % to about 2000 mol % of the substrate, for example, about 0.1 mol % to about 1500 mol %, about 0.1 mol % to about 1000 mol %, about 0.1 mol % to about 900 mol %, about 0.1 mol % to about 800 mol %, about 0.1 mol % to about 700 mol %, about 0.1 mol % to about 600 mol %, about 0.1 mol % to about 500 mol %, about 0.1 mol % to about 400 mol %, about 0.1 mol % to about 300 mol %, about 0.1 mol % to about 200 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %.

In some embodiments of the process, the liquid medium comprises an oxygen acid, such as those described herein.

In some embodiments, the oxygen acid is an electron-deficient alcohol, an aryl alcohol, or a combination thereof. As used herein, the term "electron-deficient alcohol" refers to any alcohol with at least one electron withdrawing substituent, as described herein. For example, the electron-deficient alcohol can be trifluoroethanol. As used herein, the term "aryl alcohol" refers to any alcohol with an aryl group, as described herein. For example, the aryl alcohol can be phenol.

In further embodiments, all or a portion of the oxygen acid is added as an anhydride of the oxygen acid. In preferred embodiments, a portion of the oxygen acid is added as an anhydride. Without wishing to be bound by any particular theory, it is believed that the anhydride can act as a water scavenger, resulting in a reduced amount of water in the liquid medium and in turn generating two molecules of the oxygen acid for every one molecule of water and anhydride.

The oxygen acid can be present in an amount of about 0.1 mol % of the oxidizing electrophile or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxygen acid can be present in an amount of about 2000 mol % of the oxidizing electrophile or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or can be used alone to define an open-ended range. Thus, the oxygen acid can be present in an amount between about 0.1 mol % to about 2000 mol % of the oxidizing electrophile, for example, about 0.1 mol % to about 1500 mol %, about 0.1 mol % to about 1000 mol %, about 0.1 mol % to about 900 mol %, about 0.1 mol % to about 800 mol %, about 0.1 mol % to about 700 mol %, about 0.1 mol % to about 600 mol %, about 0.1 mol % to about 500 mol %, about 0.1 mol % to about 400 mol %, about 0.1 mol % to about 300 mol %, about 0.1 mol % to about 200 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %.

The process for oxidizing a substrate comprises any suitable form of oxidation. For example, the process can be an oxidation, an oxygenation, an oxidative cleavage, an oxidative dehydration, an oxidative elimination, or any combination thereof. In certain embodiments, the process for oxidizing a substrate will produce an oxidized substrate through an oxidation, an oxygenation, or a combination thereof. It will be understood to a person of ordinary skill in the art that these oxidation and/or oxygenation products can undergo subsequent reactions during the process. For example, the oxidized substrate can undergo oxidative cleavage, oxidative dehydration, oxidative elimination, or a combination thereof. In some embodiments, the oxidized substrate can be further reacted through a substitution, dehydration, elimination, oxidation, and/or reduction reaction.

The substrate can be any suitable substrate. Typically, any compound other than the non-oxidizable liquid can be the target of the oxidation process described herein. In some embodiments, the substrate is an aliphatic compound, a heteroaliphatic compound, an aromatic compound, a heteroaromatic compound, or a combination thereof, each of which is described herein. In certain embodiments, the substrate is an alkane, alkene, alkyne, cycloalkane, heterocycloalkene, cycloalkene, heterocycloalkene, arene, heteroarene, amine, imine, alcohol, ether, aldehyde, acid, ester, thiol, thioether, or a combination thereof.

The oxidized substrate produced in step (a) of the process can be any suitable oxidized intermediate. Generally, the oxidized intermediate is any compound formed through the process of an oxidation, an oxygenation, or a combination thereof. In certain embodiments, the oxidized substrate has undergone a displacement and/or dehydration with an oxygen acid to produce a modified product, such as an ester. In certain embodiments, the oxidized substrate has undergone a hydration reaction to produce a modified product, such as an alcohol, a diol, or a polyol comprising three or more hydroxyl groups. In certain instances, the oxidized intermediate is oxidized in at least one position, for example, the oxidized intermediate can be oxidized in two different positions or more, three different positions or more, four different positions or more, or five different positions or more. In some embodiments, the oxidized intermediate has been oxidized in two or more (e.g., 3 or more, 4 or more, or 5 or more) different positions with the same functional group. In other embodiments, the oxidized intermediate has been oxidized in two or more (e.g., 3 or more, 4 or more, or 5 or more) different positions with at least two different functional groups. In preferred embodiments, the oxidized substrate has been oxidized in two different positions with the same functional group. Typically, the oxidized substrate comprises one or more alcohol functionalities, one or more ester functionalities, or a combination thereof.

In some embodiments, the oxidized intermediate is an alkyl electrophile intermediate. As used herein, the term "alkyl electrophile intermediate" refers to an intermediate where the oxidizing electrophile has undergone an electrophilic C—H activation ("CHA") reaction to produce a metal-carbon bond. Without wishing to be bound by any particular theory, it is believed that the alkyl electrophile intermediate can proceed to form an oxidized substrate.

The oxidized substrate can be any suitable oxidized substrate, or can be converted to any other suitable oxidized substrate. Generally, the oxidized substrate is any compound formed through the process of an oxidation, an oxygenation, an oxidative cleavage, an oxidative dehydration, an oxidative elimination, or any combination thereof. In some embodiments, the oxidized substrate can be, or can be converted to, an alkene, alkyne, cycloalkene, heterocycloalkene, heteroarene, amine, imine, amide, imide, carbamate, alcohol, ether, aldehyde, ketone, carboxylic acid, ester, thiol, thioether, sulfamate, thioester, sulfoxide, sulfone, sulfonic acid, or a combination thereof. In certain embodiments, the oxidized substrate has undergone a displacement and/or dehydration with an oxoacid to produce a modified product, such as an ester. In some embodiments, the oxidized substrate has been oxidized at least 1 time, for example, at least 2 times, at least 3 times, at least 4 times, or at least 5 times. In certain embodiments, the oxidized substrate is oxidized at multiple positions to form oxidized substrates, such as a diol or diene. In certain instances, the oxidized substrate is oxidized in at least one position, for example, the oxidized substrate can be oxidized in two different positions or more, three different positions or more, four different positions or more, or five different positions or more. In some embodiments, the oxidized substrate has been oxidized in two different positions or more with the same functional group, for example, two of the same functional groups or more, three of the same functional groups or more, four of the same functional groups or more, or five of the same functional groups or more. In some embodiments, the oxidized substrate has been oxidized in two different positions or more with at least two different functional groups, for example, three different functional groups or more, four different functional groups or more, or five different functional groups or more. In certain embodiments, the oxidized substrate is oxidized multiple times at the same position to form products, such as an alcohol and subsequently an aldehyde and acid.

In some embodiments, the process comprises separating one or more components from the liquid medium and/or composition. The one or more components can be separated by any suitable means, such as by filtration, distillation, flashing, rectifying, stripping, evaporation, absorption, adsorption, column chromatography, crystallization, centrifugation, extraction, recrystallization, membrane separation, or any combination thereof.

Distillation can be used to separate components of the liquid medium and/or composition based on differences in the volatilities of the mixture components. A distillation process may optionally include a chemical reaction. An example of distillation is the removal of water and glycol products from a mixture of higher boiling components including an oxidizing electrophile in solution.

Flashing can be used to remove one or more light components from the liquid medium and/or composition. Flashing is the partial vaporization that occurs when the pressure of a liquid stream is reduced. A typical flashing process includes a flow restriction such as a control valve followed by a vessel (i.e. flash drum) to allow for de-entrainment of liquid from a gas stream. Additional heating or cooling is optional. A flashing operation can be combined with one or more chemical reactions. Upon flashing, the vapor phase is richer in the more volatile components compared to the remaining liquid phase. An adiabatic flashing process results in lower temperatures of outlet streams in comparison to the inlet feed. An example of flashing is the removal of light hydrocarbons, dissolved gases, and a portion of the light components from a liquid mixture that includes a metal (e.g., thallium) species in solution.

Rectifying can be used to remove one or more heavier components from a vapor stream by contacting with a liquid stream. The less volatile components concentrate in the liquid stream. It is possible to contact the two streams by using a packed column, trayed column, bubble column, or centrifugal contactor. Flows can be co-current or counter-current. Rectifying can optionally be combined with chemical reactions. An example of rectifying is the removal of ester reaction products from a vapor stream by contacting with a liquid stream.

Stripping can be used to remove one or more lighter components from a liquid stream by contacting with a vapor stream. The more volatile components concentrate in the vapor stream. It is possible to contact the two streams by using a packed column, frayed column, bubble column, or centrifugal contactor. Flows can be co-current or counter-current. Vapor streams used for stripping could include steam, air, nitrogen, process streams, and/or other suitable species to achieve the desired separation. Stripping can optionally be combined with chemical reactions. An example of stripping is the removal of lighter reaction products from the liquid phase by contacting with a gas stream.

Evaporation can be used to remove lighter components by vaporization at a liquid/vapor interface. Evaporator designs may include falling film, rising film, wiped film, plate, and multi-effect evaporators. An evaporation process can optionally be combined with one or more chemical reactions. An example of an evaporation process is the removal of acetic acid and water from a mixture of heavier liquid components, including an antimony species in solution.

Absorption (scrubbing) can be used to selectively dissolve one or more components of a gas mixture into a liquid phase. It is possible to contact the two streams by using a packed column, frayed column, bubble column, or centrifugal contactor. If a chemical reaction occurs, the process is called chemical absorption. The liquid is selected to target the desired separation. An example of absorption is the removal of water from a vapor recycle stream by contacting with a glycol mixture.

Adsorption can be used to selectively remove one or more components of a stream based on physical or chemical interactions with a solid surface. If a chemical reaction occurs, the process is called chemisorption. The solid is selected to target the desired separation. An example of adsorption is the removal of water from a liquid recycle stream using a narrow-pore silica.

Extraction (partitioning) can be used to selectively remove one or more components from a liquid phase by contacting with a second liquid phase. Due to differences in solubilities in the two liquid phases, there can be a net transfer of species from one phase to the other. An extraction process can optionally be combined with chemical reactions. An example of extraction is contacting reactor effluent with a secondary phase that selectively dissolves a specific reaction product.

Membrane separations can be used to selectively remove one or more components from a fluid stream including gases and liquids. For example, pervaporation is a process for separating one or more components from a liquid stream by partial vaporization through a porous or non-porous membrane. Vapor permeation is a process for separating one or more components from a vapor stream by utilizing a porous or non-porous membrane. The membrane materials are selected based on their different permeabilities for different components. Membrane separations can optionally be combined with chemical reactions. An example of membrane separation is the removal of water from the organic reaction mixture using a selective ceramic membrane.

The above processes can be combined to separate components of the liquid medium and/or composition, for example, membrane distillation or extractive distillation.

In some embodiments, the process comprises (b) separating the oxidized substrate and the reduced form of the oxidizing electrophile. The oxidized substrate and the reduced form of the oxidizing electrophile can be separated by any suitable method, such as the methods described herein. For example, the oxidized substrate and the reduced form of the oxidizing electrophile can be separated by distillation.

In some embodiments, the process further comprises (c) contacting the reduced form of the oxidizing electrophile and any suitable oxidizing regeneration reagent to regenerate the oxidizing electrophile. Typically, the term "oxidant" is used in the context of generating the oxidizing electrophile and the phrase "oxidizing regeneration reagent" is used in the context of regenerating the oxidizing electrophile. However, the oxidant and the oxidizing regeneration reagent can be used interchangeably, and refer to a chemical moiety used to convert the reduced faun of the oxidizing electrophile to the oxidizing electrophile. The oxidizing regeneration reagent can be the same as or different from the oxidant. Suitable oxidizing regeneration reagents and oxidants are described herein.

In some embodiments, step (c) is an electrochemical process. As used herein, an "electrochemical process" refers to a process comprising electron transfer to or from a molecule or ion using, for example, an electric current and/or an external voltage.

Thus, the process for oxidizing the substrate can comprise the oxidizing regeneration reagent, the oxidant, both the oxidizing regeneration reagent and the oxidant, or neither the oxidizing regeneration reagent nor the oxidant. In some embodiments, the process for oxidizing the substrate comprises neither the oxidizing regeneration reagent nor the oxidant. Accordingly, the oxidizing regeneration reagent and the oxidant can be present in an amount of 0 mol % (e.g., below the level of detection) of the main group element.

In other embodiments, the oxidizing regeneration reagent and/or the oxidant are present in the liquid medium. The amount of the oxidizing regeneration reagent and/or the oxidant is not particularly limited such that a sufficient amount of the oxidizing electrophile is maintained to oxidize the substrate. Accordingly, the oxidizing regeneration reagent and/or the oxidant can be present in an amount of about 0.1 mol % of the substrate or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxidizing regeneration reagent and/or the oxidant can be present in an amount of about 2000 mol % of the substrate or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used alone to define an open-ended range.

In some embodiments, the reduced form of the oxidizing electrophile and the oxidizing regeneration reagent are contacted to regenerate the oxidizing electrophile in the presence of an oxidative regeneration catalyst. The oxidative regeneration catalyst can be any suitable catalyst, such as an oxidative regeneration catalyst that comprises copper, silver, iron, cobalt, manganese, nickel, chromium, vanadium, or a combination thereof.

In certain embodiments, the oxidizing regeneration reagent oxidizes the reduced form of the oxidizing electrophile to the oxidizing electrophile in the liquid medium in the presence of the substrate. In certain embodiments, the oxidizing regeneration reagent oxidizes the reduced form of the oxidizing electrophile to the oxidizing electrophile in a separate reactor, and is added back to the liquid medium. Accordingly, the regenerated oxidizing electrophile can be recycled for use in step (a), as described herein.

The process for oxidizing a substrate can further comprise recycling any of the components that are not consumed in the process, to be reused in the process (e.g., recycling to be reused in the liquid medium and/or the oxidizing composition). For example, the substrate, oxidizing electrophile, non-oxidizable liquid, additive, or any combination thereof can be recycled and reused in the process.

In some instances, the process for oxidizing a substrate comprises the oxidizing electrophile and/or the reduced form of an oxidizing electrophile, and liquid medium as a heterogeneous mixture or a homogenous mixture.

As used herein, the phrase "homogeneous mixture" refers to a uniform composition containing one or more phases, e.g., liquid/liquid, liquid/solid, liquid/gas, or liquid/solid/gas. Thus, a homogeneous mixture comprising a liquid can also contain a gas and/or a solid, only if the gas and/or the solid is soluble in the liquid as to form a uniform composition. In embodiments where the composition and/or the liquid medium is a homogeneous mixture, the oxidizing electrophile and/or the reduced form of an oxidizing electrophile are soluble in the liquid medium.

In preferred embodiments, the composition and/or the liquid medium is a homogeneous mixture. In other preferred embodiments, the composition and/or the medium is a heterogeneous mixture, wherein any component can be insoluble in the composition and/or the liquid medium, as long as the oxidizing electrophile maintains a certain level of solubility. Without wishing to be bound by any particular theory, it is believed that the reaction is more efficient when at least the oxidizing electrophile is soluble in the composition and/or the liquid medium. In some embodiments, the composition and/or the liquid medium can transition from a homogeneous mixture to a heterogeneous mixture and from a heterogeneous mixture to a homogeneous mixture at any point during the process.

The process for oxidizing a substrate can be carried out in a single reactor or carried out in at least 2 reactors (e.g., at least 3 or at least 4 reactors). When the process is carried out in a single reactor and the oxidizing electrophile is present in at least a stoichiometric quantity, the process for oxidizing a substrate does not necessitate regeneration of the oxidizing electrophile. In this embodiment, the process for oxidizing a substrate can be carried out under a single set of conditions in the single reactor.

Alternatively, the process for oxidizing a substrate can be carried out in a single reactor, in which the reactor is operated under conditions suitable for the oxidation of the substrate using the oxidizing electrophile and simultaneous regeneration of the oxidizing electrophile by contacting the electrophile reduction product and the oxidizing regeneration reagent. For example, when the oxidizing electrophile is depleted, the oxidizing regeneration reagent, optionally in the presence of an oxidative regeneration catalyst, is present in the liquid medium to regenerate the oxidizing electrophile.

In some embodiments, the process for oxidizing a substrate can be carried out in a single reactor in a sequential manner. In this embodiment, the reactor can be operated first under conditions suitable for the oxidation of the substrate using the oxidizing electrophile, then subsequently operated under conditions suitable for regeneration of the oxidizing electrophile by contacting the electrophile reduction product and the oxidizing regeneration reagent. For example, the oxidizing electrophile can be immobilized within the reactor, in which first a mixture comprising the substrate is circulated, then, when the oxidizing electrophile is depleted, a mixture comprising the oxidizing regeneration reagent, optionally in the presence of an oxidative regeneration catalyst, is circulated to regenerate the oxidizing electrophile.

Figure 3:
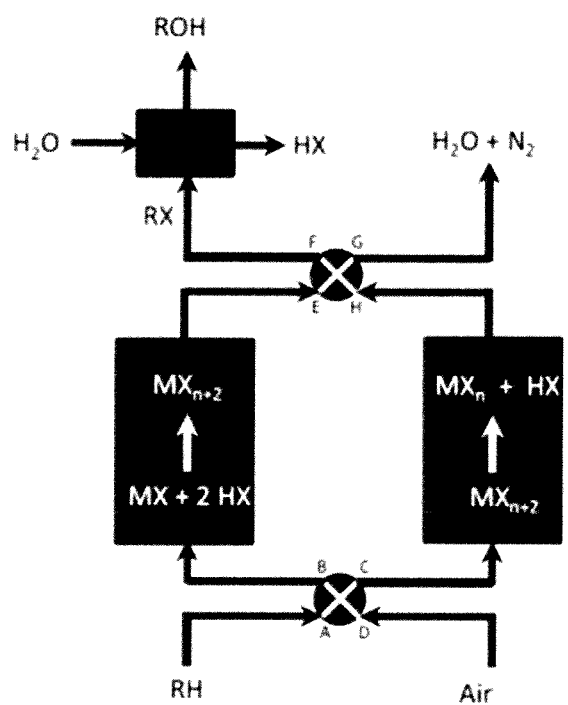
FIG. 3 illustrates an exemplary reactor for the oxidation process.

In some embodiments, the process can be carried out in a two reactor circulating liquid phase system, in which the reaction of the substrate and the oxidizing electrophile is carried out in a first reactor, and the reaction of the electrophile reduction product and the oxidizing regeneration reagent used to regenerate the oxidizing electrophile is carried out in a second reactor. An exemplary flow diagram of the two reactor process is shown in FIG. 3.

The process of the present invention can take place at any temperature suitable for forming an oxidized substrate, and ultimately, any other desired products (e.g., diol, alkene). In some embodiments, the process for oxidizing a substrate can be performed at less than about 300° C., for example, less than about 285° C., less than about 275° C., less than about 260° C., less than about 250° C., less than about 225° C., less than about 200° C., less than about 150° C., or less than about 140° C. Alternatively, or in addition to, the process for oxidizing a substrate can be performed at greater than about 50° C., for example, greater than about 70° C., greater than about 80° C., greater than about 100° C., greater than about 120° C., greater than about 140° C., greater than about 150° C., greater than about 160° C., greater than about 170° C., greater than about 180° C., greater than about 190° C., or greater than about 200° C. Any two of the foregoing endpoints can be used to define a close-ended range, or one endpoint can be used alone to define an open-ended range.

Thus, the process can be performed at a temperature between about 50° C. to about 300° C., for example, about 50° C. to about to about 275° C., about 50° C. to about 250° C., about 50° C. to about 225° C., about 50° C. to about 200° C., about 70° C. to about 200° C., about 80° C. to about 200° C., about 70° C. to about 140° C., about 100° C. to about 200° C., about 120° C. to about 200° C., about 140° C. to about 200° C., about 150° C. to about 200° C., about 160° C. to about 200° C., about 170° C. to about 200° C., about 180° C. to about 200° C., about 190° C. to about 200° C., about 200° C. to about 300° C., about 200° C. to about 350° C., about 100° C. to about 300° C., or about 150° C. to about 250° C. In some embodiments, the temperature is between about 50° C. to about 300° C., and more preferably, between about 70° C. to about 140° C.

The process of the present invention can take place at any pressure suitable for forming an oxidized substrate, and ultimately, any other desired products (e.g., diol, alkene). In some embodiments, the process for oxidizing a substrate can be performed at less than about 2000 psi (about 13800 kPa), for example, less than about 1500 psi (about 10300 kPa), less than about 1000 psi (about 6900 kPa), less than about 500 psi (about 3450 kPa), less than about 400 psi (about 2800 kPa), less than about 300 psi (about 2100 kPa), or less than about 200 psi (about 1400 kPa). Alternatively, or in addition to, the process for oxidizing a substrate can be performed at greater than about 0 psi (about 0 kPa), for example, greater than about 1 psi (about 6.9 kPa), greater than about 2 psi (about 13.8 kPa), greater than about 3 psi (about 20.7 kPa), greater than about 4 psi (about 27.6 kPa), greater than about 5 psi (about 34.5 kPa), greater than about 10 psi (about 69 kPa), or greater than about 20 psi (about 138 kPa). Any two of the foregoing endpoints can be used to define a close-ended range, or one endpoint can be used alone to define an open-ended range. Thus, the process can be performed at a pressure between about 0 psi (about 0 kPa) to about 2000 psi (about 13800 kPa), for example, about 0 psi (about 0 kPa) and about 1500 psi (about 10300 kPa), about 0 psi (about 0 kPa) and about 1000 psi (about 6900 kPa), about 0 psi (about 0 kPa) and about 500 psi (about 3450 kPa), about 0 psi (about 0 kPa) and about 400 psi (about 2800 kPa), about 0 psi (about 0 kPa) and about 300 psi (about 2100 kPa), about 0 psi (about 0 kPa) and about 200 psi (about 1400 kPa), about 2 psi (about 13.8 kPa) and about 1500 psi (about 10300 kPa), about 2 psi (about 13.8 kPa) and about 1000 psi (about 6900 kPa), about 2 psi (about 13.8 kPa) and about 500 psi (about 3450 kPa), about 2 psi (about 13.8 kPa) and about 400 psi (about 2800 kPa), about 2 psi (about 13.8 kPa) and about 300 psi (about 2100 kPa), about 2 psi (about 13.8 kPa) and about 200 psi (about 1400 kPa), about 5 psi (about 34.5 kPa) and about 1500 psi (about 10300 kPa), about 5 psi (about 34.5 kPa) and about 1000 psi (about 6900 kPa), about 5 psi (about 34.5 kPa) and about 500 psi (about 3450 kPa), about 5 psi (about 34.5 kPa) and about 400 psi (about 2800 kPa), about 5 psi (about 34.5 kPa) and about 300 psi (about 2100 kPa), or about 5 psi (about 34.5 kPa) and about 200 psi (about 1400 kPa), In some embodiments, the pressure is between about 2 psi (about 13.8 kPa) and about 500 psi (about 3450 kPa), and more preferably, between about 5 psi (about 34.5 kPa) and about 200 psi (about 1400 kPa).

The invention also provides a method of generating and/or regenerating an oxidizing electrophile comprising a main group element comprising: (a) providing a mixture comprising (i) a reduced form of an electrophile comprising a main group element, (ii) a liquid medium comprising a non-oxidizable liquid, and (iii) optionally one or more additives selected from an oxygen acid, a salt additive, a Lewis acid, and water, and (b) contacting the mixture with an oxidant to form the oxidized form of the electrophile comprising the main group element, wherein about 25% or less of the total mass of the oxidizing electrophile is an insoluble solid in the mixture. As used herein, the phrase "insoluble solid" refers to any solid that does not readily dissolve in the composition and/or the liquid medium as to form a uniform (e.g., homogeneous) composition.

In this process, the oxidizing electrophile maintains a level of solubility such that about 25% or less of the total mass of the oxidizing electrophile is an insoluble solid in the mixture (e.g., about 20% or less, about 15% or less, about 12% or less, about 10% or less, about 5% or less, or about 1% or less). Alternatively, the oxidizing electrophile can be completely soluble in the composition and/or the liquid medium (e.g., about 0% of the total mass of the oxidizing electrophile is an insoluble solid in the mixture). Thus, the oxidizing electrophile maintains a level of solubility such that about 0% to about 25% (e.g., about 0% to about 20%, about 0% to about 15%, about 0% to about 12%, about 0% to about 10%, about 0% to about 5%, or about 0% to about 1%) of the total mass of the oxidizing electrophile is an insoluble solid in the mixture.

The amount of insoluble solid can be determined by any suitable means. For example, the amount of insoluble solid can be filtered from the composition and/or the liquid medium using microfiltration (i.e., filters ranging from about 0.1 microns to about 1.0 micron). Accordingly, the percentage of total mass of the oxidizing electrophile that exists as an insoluble solid in the mixture can be determined by the mass of insoluble oxidizing electrophile filtered from the composition and/or the liquid medium using microfiltration divided by the theoretical total mass of the oxidizing electrophile in the mixture.

In some embodiments, regardless of whether the mixture is heterogeneous or homogeneous, the reduced form and oxidized form of the electrophile comprising the main group element are soluble in the liquid medium. Accordingly, the mixture is substantially free of a solid comprising the oxidizing electrophile.

In some embodiments, the method of generating and/or regenerating the oxidizing electrophile comprises heating the mixture prior to step (b). The mixture can be heated to any suitable temperature, such as those described herein.

In some embodiments, the method of generating and/or regenerating the oxidizing electrophile further comprises after step (a) and/or after step (b), a step of separating water and/or a volatile acid from the mixture. The water and/or a volatile acid can be removed from the mixture by any suitable method, including methods described herein. In certain embodiments, the water and/or a volatile acid is removed from the mixture in the presence of a volatile acid or an azeotropic additive.

In some instances, the step of contacting the mixture with an oxidant to form the oxidized form of the electrophile comprising the main group element is performed in the presence of an acid.

The invention is further illustrated by the following embodiments.

(1) An oxidizing composition comprising: (a) an oxidizing electrophile comprising a main group element in oxidized form and at least one conjugate anion of an oxygen acid; (b) a non-oxidizable liquid selected from a fluorinated hydrocarbon, a sulfone, a deactivated arene, a deactivated aliphatic, a deactivated heteroarene, a deactivated heteroaliphatic, and a combination thereof; and (c) optionally one or more salt additives of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z; and wherein the non-oxidizable liquid is substantially inert in the presence of the oxidizing electrophile.

(2) The oxidizing composition of embodiment (1), wherein the oxidizing electrophile has a formula $M^{+n}X_pL_q$, wherein M is a main group element cation in an oxidation state of n, X is the conjugate anion of an oxygen acid, L is a ligand, n is an integer from 2 to 6, p is an integer from 1 to 6, and q is an integer from 0 to 5.

(3) The oxidizing composition of embodiment (1) or (2), wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

(4) The oxidizing composition of embodiment (2) or (3), wherein each ligand is the same or different and each comprises an electron-withdrawing group.

(5) The oxidizing composition of any one of embodiments (1)-(4), comprising one or more salt additives of formula $Q_aZ_b$.

(6) The oxidizing composition of any one of embodiments (1)-(5), wherein the oxidizing electrophile comprises thallium, lead, antimony, mercury, tin, selenium, tellurium, arsenic, iodine, or bismuth.

(7) The oxidizing composition of any one of embodiments (2)-(6), further comprising an oxidizing regeneration reagent to generate and/or regenerate the oxidizing electrophile of the formula $M^{+n}X_pL_q$.

(8) The oxidizing composition of embodiment (7), wherein the oxidizing regeneration reagent is a quinone, molecular oxygen, air, a peroxide, nitric oxide, nitrous oxide, nitric acid, a nitroxide, sulfur trioxide, ozone, or a combination thereof.

(9) The oxidizing composition of embodiment (7) or (8), further comprising an oxidative regeneration catalyst to generate and/or regenerate the oxidizing electrophile of the formula $M^{+n}X_pL_q$.

(10) The oxidizing composition of embodiment (9), wherein the oxidative regeneration catalyst comprises copper, silver, iron, cobalt, manganese, nickel, chromium, vanadium, or a combination thereof.

(11) The oxidizing composition of any one of embodiments (5)-(10), wherein X and Z are the same.

(12) The oxidizing composition of any one of embodiments (5)-(10), wherein X and Z are different.

(13) The oxidizing composition of any one of embodiments (2)-(12), wherein X is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a mixture thereof.

(14) The oxidizing composition of any one of embodiments (5)-(13), wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a mixture thereof.

(15) The oxidizing composition of any one of embodiments (5)-(14), wherein Q is a proton, a cation of an alkali metal, a cation of an alkaline earth metal, a cation of a rare-earth metal, a main group element cation, or a combination thereof.

(16) The oxidizing composition of any one of embodiments (5)-(14), wherein $Q_aZ_b$ is a Lewis acid.

(17) The oxidizing composition of embodiment (15), wherein Q is a proton.

(18) The oxidizing composition of any one of embodiments (5)-(17), wherein the salt additive is an oxygen acid selected from the group consisting of aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, and a mixture thereof.

(19) A process for oxidizing a substrate, comprising: (a) contacting a substrate and (i) an oxidizing electrophile comprising a main group element in oxidized form, or (ii) an oxidant and a reduced form of the oxidizing electrophile, in a liquid medium comprising a non-oxidizable liquid and optionally one or more additives selected from an oxygen acid, a salt additive, a Lewis acid, and water, to provide an oxidized substrate and a reduced form of the oxidizing electrophile; and (b) optionally separating the oxidized substrate and the reduced form of the oxidizing electrophile.

(20) The process of embodiment (19), wherein the oxidizing electrophile has a formula $M^{+n}X_pL_q$, wherein M is a main group element cation in an oxidation state of n, X is the conjugate anion of an oxygen acid, L is a ligand, n is an integer from 2 to 6, p is an integer from 1 to 6, and q is an integer from 0 to 5.

(21) The process of embodiment (19) or (20), wherein the liquid medium comprises a salt additive of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z.

(22) The process of embodiment (20) or (21), wherein each ligand is the same or different and each comprises at least one electron-withdrawing group.

(23) The process of any one of embodiments (20)-(22), wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

(24) The process of any one of embodiments (21)-(23), wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a mixture thereof.

(25) The process of any one of embodiments (21)-(24), wherein Q is a proton, a cation of an alkali metal, a cation of an alkaline earth metal, a cation of a rare-earth metal, a main group element cation, or a combination thereof.

(26) The process of any one of embodiments (21)-(24), wherein $Q_aZ_b$ is a Lewis acid.

(27) The process of embodiment (25), wherein Q is a proton.

(28) The process of any one of embodiments (19)-(27), wherein the salt additive is an oxygen acid selected from the group consisting of aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, and a mixture thereof.

(29) The process of any one of embodiments (20)-(28), wherein X is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a mixture thereof.

(30) The process of any one of embodiments (19)-(29), wherein the oxidizing electrophile comprises thallium, lead, antimony, mercury, tin, selenium, tellurium, arsenic, iodine, or bismuth.

(31) The process of any one of embodiments (19)-(30), wherein the substrate is an aliphatic, heteroaliphatic, aromatic, heteroaromatic, or a combination thereof.

(32) The process of embodiment (31), wherein the substrate is an alkane, alkene, alkyne, cycloalkane, heterocycloalkane, cycloalkene, heterocycloalkene, arene, heteroarene, amine, imine, alcohol, ether, aldehyde, acid, ester, thiol, thioether, or a combination thereof.

(33) The process of any one of embodiments (19)-(32), wherein oxidizing a substrate is a process selected from the group consisting of oxidation, oxygenation, oxidative cleavage, oxidative dehydration, oxidative elimination, and a combination thereof.

(34) The process of any one of embodiments (20)-(33), wherein $M^{+n}X_pL_q$ undergoes reaction with the substrate in the liquid medium to yield a reduced form of the oxidizing electrophile of formula $M^{+(n-2)}X_{p-2}L_q$ or $M^{+(n-1)}X_{p-1}L_q$.

(35) The process of any one of embodiments (19)-(34), wherein the oxidizing electrophile comprising a main group element is present in at least stoichiometric quantities relative to the amount of oxidized substrate produced.

(36) The process of any one of embodiments (19)-(35), further comprising (c) contacting the reduced form of the oxidizing electrophile and an oxidizing regeneration reagent to regenerate the oxidizing electrophile.

(37) The process of embodiment (36), wherein the oxidizing regeneration reagent is a quinone, molecular oxygen, air, a peroxide, nitric oxide, nitrous oxide, nitric acid, a nitroxide, sulfur trioxide, ozone, or a combination thereof.

(38) The process of embodiment (36) or (37), wherein the reduced form of the oxidizing electrophile and the oxidizing regeneration reagent are contacted to regenerate the oxidizing electrophile in the presence of an oxidative regeneration catalyst.

(39) The process of embodiment (38), wherein the oxidative regeneration catalyst comprises copper, silver, iron, cobalt, manganese, nickel, chromium, vanadium, or a combination thereof.

(40) The process of any one of embodiments (36)-(39), wherein the oxidizing electrophile comprising a main group element in oxidized form is present in less than stoichiometric quantities relative to the oxidized substrate and acts as a catalyst.

(41) The process of any one of embodiments (19)-(39), wherein the oxidizing electrophile comprising a main group element is present in at least stoichiometric quantities relative to the amount of oxidized substrate produced.

(42) The process of any one of embodiments (19)-(41), comprising separating the oxidized substrate and the reduced form of the oxidizing electrophile.

(43) The process of any one of embodiments (19)-(42), wherein the substrate, oxidizing electrophile, non-oxidizable liquid, additive, or a combination thereof is recycled and reused in the process.

(44) A method of generating an oxidizing electrophile comprising a main group element comprising: (a) providing a mixture comprising (i) a reduced form of an electrophile comprising a main group element, (ii) a liquid medium comprising a non-oxidizable liquid, and (iii) optionally one or more additives selected from an oxygen acid, a salt additive, a Lewis acid, and water, and (b) contacting the mixture with an oxidant to form the oxidized form of the electrophile comprising the main group element, wherein about 25% or less of the total mass of the oxidizing electrophile is an insoluble solid in the mixture.

(45) The method of embodiment (44), wherein about 10% or less of the total mass of the oxidizing electrophile is an insoluble solid in the mixture.

(46) The method of embodiment (45), wherein about 5% or less of the total mass of the oxidizing electrophile is an insoluble solid in the mixture.

(47) The method of embodiment (46), wherein the mixture is substantially free of a solid comprising the main group element.

(48) The method of any one of embodiments (44)-(47), wherein the reduced form and oxidized form of the electrophile comprising the main group element are soluble in the liquid medium.

(49) The method of any one of embodiments (44)-(48), wherein the mixture is heated prior to step (b).

(50) The method of embodiment (49), further comprising after step (a) and/or after step (b), a step of separating water and/or a volatile acid from the mixture.

(51) The method of embodiment (50), wherein the separating step takes place in the presence of a volatile acid or an azeotropic additive.

(52) The method of any one of embodiments (44)-(51), wherein step (b) is performed in the presence of an acid.

(53) The method of any one of embodiments (44)-(52), wherein the oxidizing electrophile has a formula $M^{+n}X_pL_q$, wherein M is a main group element cation in an oxidation state of n, X is the conjugate anion of an oxygen acid, L is a ligand, n is an integer from 2 to 6, p is an integer from 1 to 6, and q is an integer from 0 to 5.

(54) The method of any one of embodiments (44)-(53), wherein the reduced form of the oxidizing electrophile is of formula $M^{+(n-2)}X_{p-2}L_q$ or $M^{+(n-1)}X_{p-1}L_q$, wherein M is a main group element cation in an oxidation state of n, X is the conjugate anion of an oxygen acid, L is a ligand, n is an integer from 2 to 6, p is an integer from 1 to 6, and q is an integer from 0 to 5.

(55) The method of embodiment (53) or (54), wherein the ligand is at least one monodentate or bidentate ligand that is aliphatic-based or aromatic-based and comprises at least one oxo, thiol, sulfonyl, or carboxyl group, and optionally comprises one or more electron withdrawing groups.

(56) The method of embodiment (53) or (54), wherein the ligand is a bridging oxide, a terminal oxide, hydroxide, or combination thereof.

(57) The method of embodiment (55), wherein the ligand comprises at least one carboxyl group.

(58) The method of embodiment (57), wherein the ligand is aromatic-based.

(59) The method of embodiment (58), wherein the ligand is aromatic based comprising at least one carboxyl group and at least one nitro group.

(60) The method of embodiment (55), wherein the ligand is selected from the group consisting of:

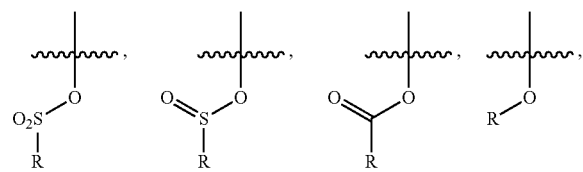

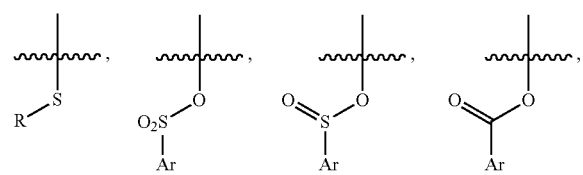

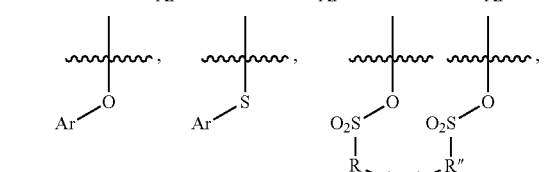

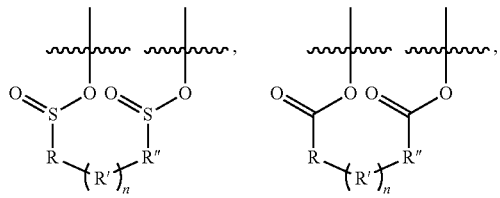

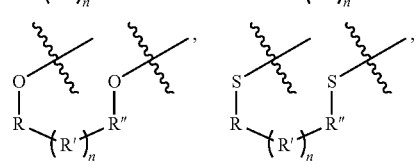

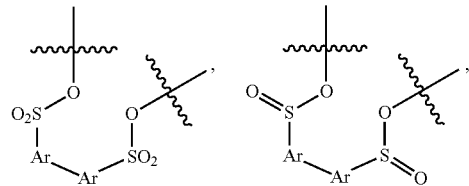

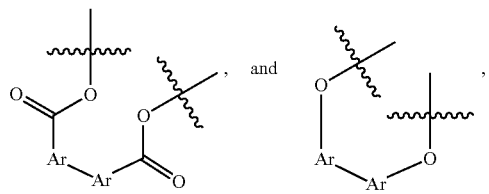

wherein R, R', and R" are the same or different and each is an optionally substituted alkyl, Ar is an optionally substituted aryl, EWG is at least one electron withdrawing group, and n is 0 or an integer of 1 to 6.

(61) The method of embodiment (53) or (54), wherein the ligand is —Ar-EWG, wherein Ar is an optionally substituted aryl and EWG is at least one electron withdrawing group.

(62) The method of embodiment (53) or (54), wherein the ligand is selected from the group consisting of:

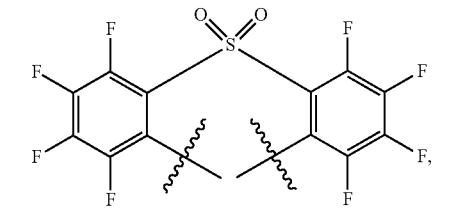

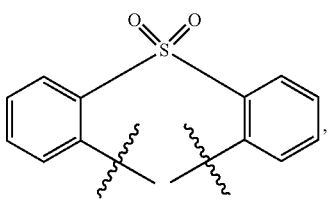

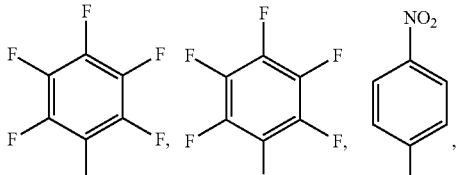

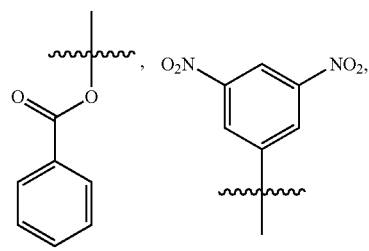

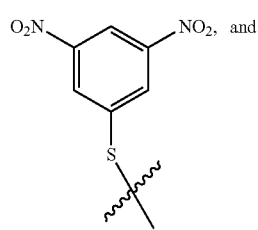

-continued

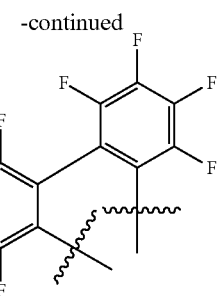

(63) The method of any one of embodiments (44)-(62), wherein the ligand is present in the mixture in less than stoichiometric quantities relative to the main group element.

(64) The method of any one of embodiments (44)-(62), wherein the ligand is present in the mixture in stoichiometric quantities relative to the main group element.

(65) The method of any one of embodiments (44)-(62), wherein the ligand is present in the mixture in at least stoichiometric quantities relative to the main group element.

(66) The method of any one of embodiments (44)-(65), wherein the reduced form of the main group electrophile comprises at least one counterion that is a conjugate anion of an oxygen acid.

(67) The method of embodiment (66), wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

(68) The method of any one of embodiments (44)-(67), wherein the main group element is selected from thallium, lead, antimony, mercury, tin, selenium, tellurium, arsenic, iodine, or bismuth.

(69) The method of any one of embodiments (44)-(68), wherein the reduced form of the oxidizing electrophile comprising the main group element comprises Sb(III), Te(IV), Te(II), Bi(III), Se(IV), Se(II), As(III), I(I), I(III), or Sn(II).

(70) The method of any one of embodiments (44)-(69), wherein the oxidant is a quinone, molecular oxygen, air, a peroxide, nitric oxide, nitrous oxide, nitric acid, a nitroxide, sulfur trioxide, ozone, or a combination thereof.

(71) The method of any one of embodiments (44)-(70), wherein the liquid medium comprises an oxygen acid.

(72) The method of embodiment (71), wherein the oxygen acid is selected from the group consisting of aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, and a mixture thereof.

(73) The method of embodiment (71), wherein all or a portion of the oxygen acid is added as an anhydride of the oxygen acid.

(74) The method of any one of embodiments (44)-(73), wherein the liquid medium comprises a non-oxidizable liquid selected from a fluorinated hydrocarbon, a sulfone, a deactivated arene, a deactivated aliphatic, a deactivated heteroarene, a deactivated heteroaliphatic, and a combination thereof, wherein the liquid is substantially inert in the presence of the oxidizing electrophile.

(75) The method of embodiment (74), wherein the non-oxidizable liquid is a sulfone or a deactivated arene.

(76) The method of any one of embodiments (44)-(75), wherein the liquid medium comprises a salt additive.

(77) The process of embodiment (76), wherein the liquid medium comprises a salt additive of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z.

(78) The process of embodiment (77), wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a mixture thereof.

(79) The process of embodiment (77) or (78), wherein Q is a proton, a cation of an alkali metal, a cation of an alkaline earth metal, a cation of a rare-earth metal, a main group element cation, or a combination thereof.

The following examples further illustrate the invention but, of course, should not be construed as in any way limiting its scope.

EXAMPLES

For quantifying substrate and product concentrations in solution by NMR, typically 100 μL of a solution containing a known concentration of an appropriate standard (e.g., dimethyl sulfone, dichloromethane, hexafluorobenzene, etc.) in the same non-oxidizable liquid as the reaction of interest, was added to the reaction solution as an internal standard. An aliquot of this reaction solution was then pipetted into a 5 mm NMR tube, the tube was capped with a standard NMR cap containing a ~2 mm hole, and then a 2 mm capillary containing $d_6$-benzene was placed into the tube through the hole. NMR spectra ($^1H$ or $^{19}F$) were then taken with >a 10 second relaxation delay (with no decoupling).

Example 1

This example demonstrates the stability of certain non-oxidizable liquids in the presence of an oxidizing electrophile in an embodiment of the invention.

Oxidizing compositions were prepared comprising a potentially non-oxidizable liquid, and an excess of thallium (III) trifluoroacetate (Tl(TFA)$_3$) in trifluoroacetic acid. The purpose was to determine if each of the liquid species is substantially inert in the presence of Tl(TFA)$_3$, the oxidizing electrophile. The oxidizing compositions were stirred at 150° C. for 3 hours. Liquid stability was measured by $^1$H NMR spectroscopy by comparing relative peak ratios of the selected liquid species before oxidation and after the 3-hour heating period. The stability of each non-oxidizable liquid species is reported as % retention of the characteristic peaks in the $^1$H NMR spectrum. The results are set forth in Table 1.

TABLE 1

| Liquid Species | Stability (% retention) |
|---|---|
| Arenes | |
| C$_6$H$_5$(CF$_3$) | 14% |
| C$_6$H$_5$(NO$_2$) | 50% |
| C$_6$H$_5$(CN) | <20% |
| m-C$_6$H$_4$(CF$_3$)$_2$ | >90% |
| p-C$_6$H$_4$(CF$_3$)$_2$ | >90% |
| m-C$_6$H$_4$(NO$_2$)$_2$ | >90% |
| p-C$_6$H$_4$(NO$_2$)$_2$ | >95% |
| m-C$_6$H$_4$(CF$_3$)(NO$_2$) | >90% |
| o-C$_6$H$_4$(CF$_3$)(NO$_2$) | >90% |
| p-C$_6$H$_4$F(NO$_2$) | 85% |
| o-C$_6$H$_4$F(NO$_2$) | <70% |
| 1,3-C$_6$H$_4$(CF$_3$)$_2$(NO$_2$) | >90% |
| Sulfoxides | |
| Dimethyl sulfone | >95% |
| Sulfolane | >95% |
| Me(SO$_2$)Et | >95% |
| Et(SO$_2$)Et | 90% |
| nPr(SO$_2$)nPr | 82% |
| nBu(SO$_2$)nBu | 84% |
| Aliphatics | |
| Et(TFA)$_2$ | >95% |
| CF$_3$CH$_2$OH | >95% |
| Heteroaliphatics | |
| CH$_3$OtBu | 0% |
| Diglyme | 31% |
| Ethylene carbonate | 0% |

TABLE 1-continued

| Liquid Species | Stability (% retention) |
|---|---|
| Heteroarenes | |
| Pyridine | 0% |
| Pyrimidine (1,3) | 75% |
| Pyrazine (1,4) | >90% |
| Quinoxoline | 60% |
| Perfluoropyridine | >80% |
| Perfluoroalkanes | |
| Perfluorooctane | >90% |
| C$_6$F$_{11}$(CF$_3$) | >80% |

TABLE 1-continued

| Liquid Species | Stability (% retention) |
|---|---|
| 1,3-C$_6$F$_{10}$(CF$_3$)$_2$ | >90% |
| Perfluorodecalin | >90% |

As is apparent from the results set forth in Table 1, certain liquids were substantially non-oxidizable, while others were not stable to the oxidizing composition. For example, arenes having a single electron withdrawing group, such as C$_6$H$_5$(CF$_3$), C$_6$H$_5$(NO$_2$), C$_6$H$_5$(CN), resulted in stabilities of less than 50%.

Example 2

This example demonstrates the stability of certain oxidation products in the presence of an oxidation composition containing a non-oxidizable liquid, thallium(III) trifluoroacetate (Tl(TFA)$_3$), and trifluoroacetic acid.

Authentic samples of certain oxidation products, namely, the mono-trifluoroacetyl ester of ethanol (Et(TFA)), the di-fluoroacetyl ester of ethylene glycol (Et(TFA)$_2$), the mono-trifluoroacetyl ester of 2-propanol (iPr(TFA)), and the di-trifluoroacetyl ester of 1,2-propanediol (iPr(TFA)$_2$) were prepared separately. Oxidizing compositions were prepared containing an oxidation product, an excess of Tl(TFA)$_3$, trifluoroacetic acid (10% by volume based on the non-oxidizable liquid), in a non-oxidizable liquid. The oxidizing compositions were stirred at 150° C. for 3 hours. Oxidation product stability was measured by $^1$H NMR spectroscopy, using characteristic non-oxidizable liquid (liquid species) peaks, by comparing relative peak ratios before oxidation and after the 3-hour heating period. Oxidation product stability is reported as % retention of the characteristic peaks in the $^1$H NMR spectrum. Formation of the di-trifluoroacetyl ester is reported in parentheses. The results are set forth in Table 2.

TABLE 2

| Oxidation product | Liquid Species | | | | |
|---|---|---|---|---|---|
| | Sulfolane | Et(TFA)$_2$ | C$_6$F$_{11}$(CF$_3$) | m-C$_6$H$_4$(CF$_3$)$_2$ | m-C$_6$H$_4$(NO$_2$)$_2$ |
| Et(TFA) | 88% | N/A | 92% | 90% | 63% (1%) |
| Et(TFA)$_2$ | 90% | N/A | 90% | 89% | 84% |
| iPr(TFA) | 66% | 67% (20%) | 55% (33%) | 48% (37%) | 47% (23%) |
| iPr(TFA)$_2$ | 91% | >80% | 90% | 87% | 74% |

As is apparent from the results set forth in Table 2, Et(TFA)$_2$ and iPr(TFA)$_2$ were stable, i.e., resulted in greater than 80% retention of the characteristic peaks in the $^1$H NMR spectrum, for all non-oxidizable liquids tested.

Example 3

This example demonstrates the oxidation of propane in the presence of an oxidation composition containing a non-oxidizable liquid, thallium(III) trifluoroacetate (Tl(TFA)$_3$), and trifluoroacetic acid.

A reactor containing Tl(TFA)$_3$, trifluoroacetic acid (10% by volume based on the non-oxidizable liquid), and a non-oxidizable liquid was charged with propane. The solution was stirred at 150° C. for 3 hours. Percent yield of the oxidation products, mono-trifluoroacetyl ester of 2-propanol ("iPr(TFA)"), and di-trifluoroacetyl ester of 1,2-propanediol ("iPr(TFA)$_2$"), were measured by $^1$H NMR spectroscopy, using characteristic peaks determined from authentic samples, by comparing relative integration of peak area ratios before oxidation and after the 3-hour heating period. Oxidation product yield is reported based on amount of Tl(TFA)$_3$ consumed in the reaction. In addition, trifluoroacetic acid (entry 26) was used as the non-oxidizable liquid (liquid species) as a comparative. The results are set forth in Table 3.

TABLE 3

| Entry | Liquid Species Class | Liquid Species | Stability (% retention from Table 1) | % Yield (based on Tl(III)) |
|---|---|---|---|---|
| 1 | Deactivated arene | m-C$_6$H$_4$(CF$_3$)$_2$ | >90% | 31% |
| 2 | Deactivated arene | p-C$_6$H$_4$(CF$_3$)$_2$ | >90% | 9% |
| 3 | Deactivated arene | m-C$_6$H$_4$(CF$_3$)(NO$_2$) | >90% | 13% |
| 4 | Deactivated arene | p-C$_6$H$_4$F(NO$_2$) | 85% | 1% |
| 5 | Deactivated arene | 1,3,5-C$_6$H$_3$(CF$_3$)$_2$(NO$_2$) | >90% | 15% |
| 6 | Deactivated heteroarene | Pyrazine | >90% | 0% |
| 7 | Deactivated heteroarene | Perfluoropyradine | >80% | 7% |
| 8 | Deactivated aliphatic | CF$_3$CH$_2$OH | >95% | 3% |
| 9 | Sulfoxide | Dimethyl sulfone (DMS) | >95% | 15% |
| 10 | Sulfoxide | Sulfolane | >95% | 2% |
| 11 | Solvent mixture | 1:1 DMS:Et(TFA)$_2$ | N/A | 65% |
| 12 | Solvent mixture | 1:3 DMS:Et(TFA)$_2$ | N/A | 87% |
| 13 | Solvent mixture | 1:1 Sulfolane:Et(TFA)$_2$ | N/A | 6% |
| 14 | Solvent mixture | 1:1 m-C$_6$H$_4$(CF$_3$)$_2$:Et(TFA)$_2$ | N/A | 60% |
| 15 | Solvent mixture | 1:1 m-C$_6$H$_4$(CF$_3$)(NO$_2$):Et(TFA)$_2$ | N/A | 13% |
| 16 | Solvent mixture | 1:1 DMS:Sulfolane | N/A | 5% |
| 17 | Solvent mixture | 1:1 DMS:Me(SO$_2$)Et | N/A | 7% |
| 18 | Solvent mixture | 1:1 DMS:p-C$_6$H$_4$(CF$_3$)$_2$ | N/A | 24% |
| 19 | Solvent mixture | 1:1 DMS:m-C$_6$H$_4$(CF$_3$)$_2$ | N/A | 25% |
| 20 | Solvent mixture | 1:1 DMS:m-C$_6$H$_4$(CF$_3$)(NO$_2$) | N/A | 26% |
| 21 | Solvent mixture | 1:1 DMS:1,3,5-C$_6$H$_3$(CF$_3$)$_2$(NO$_2$) | N/A | 25% |
| 22 | Propane oxidation product | Et(TFA)$_2$ | >95% | 93% |
| 23 | Perfluoroalkane | C$_6$F$_{11}$(CF$_3$) | >80% | 87% |
| 24 | Perfluoroalkane | 1,3-C$_6$F$_{10}$(CF$_3$)$_2$ | >90% | 81% |
| 25 | Perfluoroalkane | Perfluorodecalin | >90% | 84% |
| 26 | Acid | Trifluoroacetic acid | N/A | 95% |

As is apparent from the results set forth in Table 3, perfluoroalkanes are not only stable to the reaction conditions, but also produce oxidizing compositions capable of oxidizing propane with high yields. In addition, the oxidation product, Et(TFA)$_2$, is also proficient at facilitating the oxidation of propane (see, for example, entries 11, 12, 14, and 22).

Example 4

This example demonstrates the effect that temperature has on the oxidation of propane in the presence of an oxidation composition comprising a non-oxidizable liquid, thallium (III) trifluoroacetate (Tl(TFA)$_3$), and trifluoroacetic acid.

A reactor containing Tl(TFA)$_3$, trifluoroacetic acid (10% by volume based on the non-oxidizable liquid), and a non-oxidizable liquid was charged with propane. The non-oxidizable liquids used in this example are 1:1 DMS:p-C$_6$H$_4$(CF$_3$)$_2$ (Table 4a), 1:1 DMS:m-C$_6$H$_4$(CF$_3$)$_2$ (Table 4a), and DMS (Table 4b). The solution was stirred at either 150° C., 180° C., or 200° C. for 3 hours. Percent yield of the oxidation products, mono-trifluoroacetyl ester of 2-propanol ("iPr(TFA)") and di-trifluoroacetyl ester of 1,2-propanediol ("iPr(TFA)$_2$"), were measured by $^1$H NMR spectroscopy, using characteristic peaks determined from authentic samples, by comparing relative peak ratios before oxidation and after the 3-hour heating period. Oxidation product yield is reported based on amount of Tl(TFA)$_3$ consumed in the reaction. The results are set forth in Tables 4a and 4b.

TABLE 4a

| Entry | Liquid Species | Temperature (° C.) | % Yield (based on Tl(III)) |
|---|---|---|---|
| 1 | 1:1 DMS:p-C$_6$H$_4$(CF$_3$)$_2$ | 150 | 24% |
| 2 | 1:1 DMS:m-C$_6$H$_4$(CF$_3$)$_2$ | 150 | 25% |
| 3 | 1:1 DMS:p-C$_6$H$_4$(CF$_3$)$_2$ | 180 | 93% |
| 4 | 1:1 DMS:m-C$_6$H$_4$(CF$_3$)$_2$ | 180 | 35% |

TABLE 4b

| Entry | Liquid Species | Temperature (° C.) | % Yield (based on Tl(III)) |
|---|---|---|---|
| 1 | DMS | 150 | 12% |
| 2 | DMS | 180 | 65% |
| 3 | DMS | 200 | 44% |

As is apparent from the results set forth in Tables 4a and 4b, the oxidation of propane is temperature dependent. Heating the solution to 180° C. provided the highest yields for the non-oxidizable liquids tested in Tables 4a and 4b.

Example 5

This example demonstrates the effect that an additive has on the oxidation of propane in the presence of an oxidation composition comprising a non-oxidizable liquid, thallium (III) methanesulfonate (Tl(OMs)$_3$), and an additive.

A reactor containing 200 mM Tl(OMS)$_3$ in dimethylsulfone (DMS), and an additive was charged with propane. The solution was stirred at 165° C. for 3 hours. The additives used in this example were methanesulfonic acid (MsOH) and sodium methanesulfonate (NaOMs). Percent yield of the oxidation products (which predominantly consisted of the diester (>95%), mono-methanesulfonate ester of 2-propanol ("iPr(OMs)") and di-methanesulfonate ester of 1,2-propanediol ("iPr(OMs)$_2$"), were measured by $^1$H NMR spectroscopy, using characteristic peaks determined from authentic samples, by comparing relative peak ratios before oxidation and after the 3-hour heating period. Oxidation product yield is reported based on amount of Tl(OMs)$_3$ consumed in the reaction. The results are set forth in Table 5.

TABLE 5

| Entry | Additive | | % Yield |
| | MsOH (mM) | NaOMs (mM) | (based on Tl(III)) |
| --- | --- | --- | --- |
| 1 | 500 | 0 | 21% |
| 2 | 250 | 0 | 30% |
| 3 | 100 | 0 | 41% |
| 4 | 0 | 0 | 5% |
| 5 | 300 | 200 | 56% |
| 6 | 200 | 200 | 47% |
| 7 | 100 | 200 | 59% |
| 8 | 0 | 200 | 59% |
| 9 | 200 | 500 | 51% |
| 10 | 200 | 1000 | 49% |

As is apparent from the results set forth in Table 5, the oxidation of propane does not require an additive to proceed (see, for example, entry 4). As is evident from entry 8, the oxidation does not require an acid additive to be high yielding. Buffered systems, comprising acid and a salt, also produced high yields (see, for example, entries 5-7, 9, and 10).

Example 6

This example demonstrates the oxidation of propylene in the presence of an oxidation composition comprising a non-oxidizable liquid, an Sb(V) species, and an additive.

A reactor containing an Sb(V) species, sulfolane, and an additive was charged with propylene. The Sb(V) species used in this example was generated in situ by the addition of 50% hydrogen peroxide to an Sb(III) species and acetic anhydride in sulfolane. The solution was stirred at either 130° C., 150° C., 170° C., or 190° C. for 1 or 3 hours. Percent yield of the oxidation product, di-ester of 1,2-propanediol, was measured by $^1$H NMR spectroscopy, using characteristic peaks determined from authentic samples, by comparing relative peak ratios before oxidation and after the 1- or 3-hour heating period. Oxidation product yield is reported based on amount of hydrogen peroxide added to the reaction. The results are set forth in Table 6.

TABLE 6

| Entry | Additive | [Additive] (mM) | Temperature (° C.) | % Yield (based on Sb(V)) | |
| | | | | After 1 hr | After 3 hr |
| --- | --- | --- | --- | --- | --- |
| 1 | KOAc | 100 | 130-190 | <1% | <1% |
| 2 | KOMs | 100 | 130 | <1% | <10% |
| 3 | KOMs | 100 | 150 | <5% | 20% |
| 4 | KOMs | 100 | 170 | 20% | 40% |
| 5 | KOMs | 100 | 190 | 20% | 20% |

As is apparent from the results set forth in Table 6, the oxidizing composition also oxidizes propylene in the absence of a strong acid (see, for example, entries 4 and 5).

Example 7

The substrate (e.g., phenylacetylene, benzaldehyde, benzyl alcohol, toluene, anisole, benzyl ether) was dissolved in the corresponding non-oxidizable liquid (liquid species) to yield a 0.5 M solution. The oxidant (e.g., Tl(X)$_3$, Pb(X)$_4$, C$_6$F$_5$I(X)$_2$, Sb(X)$_3$ and H$_2$O$_2$, Te(X)$_6$, and Hg(X)$_2$) was dissolved in the corresponding liquid species to yield a 0.2 M solution. "X" is as defined in FIGS. 4A-4C. 2.0 mL of the oxidant solution was added to a 2-5 ml microwave vial equipped with a stir bar. The substrate solution (2.0 mL) was added to the microwave vial. The additives (if present) were added to the reaction and the crimp seal cap was sealed to the top of the vial. For gaseous substrates (e.g., propane, ethane, and methane), the reaction vial was charged with the gaseous substrate prior to sealing. In FIGS. 4A-4C, the following abbreviations are used: DMS—dimethyl sulfone; MsOH—methanesulfonic acid; MNB-H—meta-nitrobenzoic acid; and TCE—tetrachloroethane.

For the preparation of the Sb(TFA)$_3$ and H$_2$O$_2$ solution, the following procedure was followed. Sb(TFA)$_3$ and additives (except anhydrides) were dissolved in TFAH (10% less than total theoretical volume) in a vial and the solution was cooled with an ice bath. The 50% H$_2$O$_2$ in H$_2$O was added to the solution and stirred for 10 min. The anhydride was added, the vial was capped, and stirred for 10 min at room temperature. The solution was opened and TFAH was added to achieve desired final volume to give the correct Sb concentration.

The vials were placed into a preheated aluminum block set to the appropriate temperature (100-200° C.). The reactions were stirred at temperature for 1 h. The vials were removed from the heat and cooled to room temperature. 1.0 ml of the solutions were added to a 1-dram vial and a standard was added to the solution. A sample of the solution was added to an NMR tube equipped with a capillary containing d$_6$-benzene. Quantitative NMR spectra were acquired for each sample. The results are set forth in FIGS. 4D-4G.

As is apparent from the results set forth in FIGS. 4D-4G, the non-oxidizable liquids (liquid species) are not only stable to the reaction conditions, but also produce oxidizing compositions capable of oxidizing a range of substrates (e.g., alkanes, alkynes, aldehydes, alcohols, arenes, ethers, amines, thiols, and thioethers).

Example 8

The following example is a general procedure for oxidizing a reduced form of the oxidizing electrophile with an oxidant.

The solid metal salt or metal oxide (e.g., Sb(OAc)$_3$, Sn(OAc)$_2$, Sb$_2$O$_3$, SnO, etc.) and ligand (L) were placed into a flask equipped with a stir bar. The solids were dissolved into the liquid medium (e.g., trifluoroacetic acid, sulfolane). In some instances, the mixture was heated to dissolve the solids. If desired, volatile ligand (e.g., HOAc, H$_2$O) could be removed via distillation to yield the corresponding M-L complex.

The resulting solution was then oxidized through the dropwise addition of oxidant (e.g., 50% H$_2$O$_2$ solution) and rapid stirring. The solution was cooled and the oxidation state of the resulting solid showed high conversion (>90%) of the metal (M-L) oxidized to the higher oxidation state (M$^{2+}$-L). The oxidation can be performed in the presence or absence of acid (e.g., AcOH) or other additives. If included, anhydride was added after oxidation and after all other additives were added.

The various electrophiles tested and the reaction conditions are set forth in the table of FIG. 5. For control experiments, the same steps were followed except for the addition of an oxidant. See, for example, entries 85-87 and 94-96 in FIG. 5.

The presence or absence of solids in the liquid medium was qualitatively observed at the time points of: pre-oxidation, post-oxidation, and after anhydride treatment. When no solids were observed, the electrophile was considered to be soluble, as indicated by "Y" for yes in FIG. 5. When solids were observed, the mixture was denoted with "N" for no in FIG. 5. In FIG. 5, the following abbreviations are used: MNB-H—meta-nitrobenzoic acid; PNB-H—para-nitrobenzoic acid; and DNB-H—3,5-dinitrobenzoic acid.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. An oxidizing composition comprising:
(a) an oxidizing electrophile comprising a main group element in oxidized form and at least one conjugate anion of an oxygen acid;
(b) a non-oxidizable liquid selected from a fluorinated hydrocarbon, a sulfone, a deactivated arene, a deactivated aliphatic, a deactivated heteroarene, a deactivated heteroaliphatic, compound (I), and a combination thereof;

wherein
the deactivated arene and deactivated heteroarene comprise at least one electron withdrawing group selected from the group consisting of $-NO_2$, fluoro-$C_{1-8}$ alkyl, $-F$, $-OOCR$, $-COOH$, $-OH_2^+$, $-CONH_2$, $-COOR$, $-NR_3^+$, $-CN$, $-SO_3H$, $-SO_3R$, $-SO_3W$, and a combination thereof,
the deactivated aliphatic and deactivated heteroaliphatic comprise at least one electron withdrawing group selected from the group consisting of $-NO_2$, $-CONH_2$, $-NR_3^+$, $-CN$, $-SO_3H$, $-SO_3R$, $-SO_3W$, and a combination thereof, provided that the deactivated aliphatic and deactivated heteroaliphatic are not methanesulfonic acid,
R is hydrogen or any aliphatic, heteroaliphatic, aromatic, or heteroaromatic moiety, each of which is optionally substituted with halo, hydroxyl, cyano, nitro, alkoxy, amino, aryl, heteroaryl, alkyl, heteroalkyl, oxo, or a combination thereof, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, and an alkaline earth metal, and
compound (I) is selected from trifluoromethanol, trifluoromethyl 2,2,2-trifluoroacetate, 2,2,2-trifluoroethan-1-ol, 2,2,2-trifluoroethyl 2,2,2-trifluoroacetate, perfluoroethyl 2,2,2-trifluoroacetate, 1,1,2,2,2-pentafluoroethan-1-ol, trifluoro(nitro)methane, 1,1,2,2-tetrafluoroethane-1,2-diol, 1,1,2,2-tetrafluoro-2-hydroxyethyl 2,2,2-trifluoroacetate, perfluoroethane-1,2-diyl bis(2,2,2-trifluoroacetate), 1,1,2,2,3,3-hexafluoropropane-1,3-diol, propane-1,2,3-triyl tris(2,2,2-trifluoroacetate), oxalic acid, 1,1,1,4,4,4-hexafluorobutane-2,3-dione, methyl 2,2,3,3,3-pentafluoropropanoate, trifluoromethyl 2,2,3,3,3-pentafluoropropanoate, trifluoromethyl acetate, 1,1-difluoroethyl acetate, 2,2,2-trifluoroethyl acetate, perfluoroethyl acetate, perfluoropropan-2-yl acetate, 1,1,1,3,3,3-hexafluoropropan-2-yl acetate, 1,1,2,2-tetrafluoro-2-hydroxyethyl acetate, perfluoroethane-1,2-diyl diacetate, ethane-1,2-diyl diacetate, propane-1,2,3-triyl trisacetate, perfluoropropane-1,2,3-triyl triacetate, 1,1,3,3-tetrafluoropropane-1,2,3-triyl triacetate, 1,1-difluoroethane-1,2-diyl diacetate, trifluoro(trifluoromethoxy)methane, 1,1,1,2,2-pentafluoro-2-(trifluoromethoxy)ethane, 1,1,1,2,2-pentafluoro-2-(perfluoroethoxy)ethane, tris(trifluoromethyl)amine, 1,1,2,2,2-pentafluoro-N-(perfluoroethyl)-N-(trifluoromethyl)ethan-1-amine, tris(perfluoroethyl)amine, 2,2,2-trifluoro-N,N-bis(trifluoromethyl)acetamide, NN-bis(trifluoromethyl)formamide, 2,2,2-trifluoroacetamide, perfluoropyrrolidine, perfluoropyrroline, perfluoropyran, perfluoropiperidine, perfluorodioxane, perfluoromorpholine, perfluoropiperazine, pyrrolidine carboxylic acid, pyrroline carboxylic acid, pyran carboxylic acid, piperidine carboxylic acid, dioxane carboxylic acid, morpholine carboxylic acid, piperazine carboxylic acid, and a combination thereof, and
(c) optionally one or more salt additives of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z; and
wherein the non-oxidizable liquid is substantially inert in the presence of the oxidizing electrophile.

2. The oxidizing composition of claim 1, wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

3. The oxidizing composition of claim 1, comprising one or more salt additives of formula $Q_aZ_b$.

4. The oxidizing composition of claim 1, wherein the oxidizing electrophile comprises thallium, lead, antimony, mercury, tin, selenium, tellurium, arsenic, iodine, or bismuth.

5. The oxidizing composition of claim 1, wherein the oxidizing electrophile has a formula $M^{+n}X_pL_q$, wherein M is a main group element cation in an oxidation state of n, X is the conjugate anion of an oxygen acid, L is a ligand, n is an integer from 2 to 6, p is an integer from 1 to 6, and q is an integer from 0 to 5.

6. The oxidizing composition of claim 5, further comprising an oxidizing regeneration reagent to generate and/or regenerate the oxidizing electrophile of the formula $M^{+n}X_pL_q$, wherein the oxidizing regeneration reagent is a quinone, molecular oxygen, air, a peroxide, nitric oxide, nitrous oxide, nitric acid, a nitroxide, sulfur trioxide, ozone, or a combination thereof.

7. The oxidizing composition of claim 6, further comprising an oxidative regeneration catalyst to generate and/or regenerate the oxidizing electrophile of the formula $M^{+n}X_pL_q$.

8. The oxidizing composition of claim 7, wherein the oxidative regeneration catalyst comprises copper, silver, iron, cobalt, manganese, nickel, chromium, vanadium, or a combination thereof.

9. The oxidizing composition of claim 3, wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a mixture thereof.

10. The oxidizing composition of claim 3, wherein Q is a proton, a cation of an alkali metal, a cation of an alkaline earth metal, a cation of a rare-earth metal, a main group element cation, or a combination thereof.

11. The oxidizing composition of claim 3, wherein the salt additive is an oxygen acid selected from the group consisting of aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, and a mixture thereof.

12. A process for oxidizing a substrate, comprising:
(a) contacting a substrate and the oxidizing composition of claim 1 to provide an oxidized substrate and a reduced form of the oxidizing electrophile; and
(b) optionally separating the oxidized substrate and the reduced form of the oxidizing electrophile.

13. The process of claim 12, wherein the oxidizing composition comprises a salt additive of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z.

14. The process of claim 13, wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

15. The process of claim 13, wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a mixture thereof.

16. The process of claim 13, wherein Q is a proton, a cation of an alkali metal, a cation of an alkaline earth metal, a cation of a rare-earth metal, a main group element cation, or a combination thereof.

17. The process of claim 13, wherein the salt additive is an oxygen acid selected from the group consisting of aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, and a mixture thereof.

18. The process of claim 12, wherein the oxidizing electrophile comprises thallium, lead, antimony, mercury, tin, selenium, tellurium, arsenic, iodine, or bismuth.

19. The process of claim 12, wherein the substrate is an aliphatic, heteroaliphatic, aromatic, heteroaromatic, or a combination thereof.

20. The process of claim 12, further comprising (c) contacting the reduced form of the oxidizing electrophile and an oxidizing regeneration reagent to regenerate the oxidizing electrophile.

21. The process of claim 20, wherein the oxidizing regeneration reagent is a quinone, molecular oxygen, air, a peroxide, nitric oxide, nitrous oxide, nitric acid, a nitroxide, sulfur trioxide, ozone, or a combination thereof.

22. The process of claim 20, wherein the reduced form of the oxidizing electrophile and the oxidizing regeneration reagent are contacted to regenerate the oxidizing electrophile in the presence of an oxidative regeneration catalyst.

23. The process of claim 22, wherein the oxidative regeneration catalyst comprises copper, silver, iron, cobalt, manganese, nickel, chromium, vanadium, or a combination thereof.

24. The process of claim 12, wherein the oxidizing electrophile has a formula $M^{+n}X_pL_q$, wherein M is a main group element cation in an oxidation state of n, X is the conjugate anion of an oxygen acid, L is a ligand, n is an integer from 2 to 6, p is an integer from 1 to 6, and q is an integer from 0 to 5.

25. The process of claim 24, further comprising (c) contacting the reduced form of the oxidizing electrophile and an oxidizing regeneration reagent to regenerate the oxidizing electrophile of the formula $M^{+n}X_pL_q$.

26. The process of claim 25, wherein the oxidizing regeneration reagent is a quinone, molecular oxygen, air, a peroxide, nitric oxide, nitrous oxide, nitric acid, a nitroxide, sulfur trioxide, ozone, or a combination thereof.

27. The process of claim 25, wherein the reduced form of the oxidizing electrophile and the oxidizing regeneration reagent are contacted to regenerate the oxidizing electrophile in the presence of an oxidative regeneration catalyst.

28. The process of claim 27, wherein the oxidative regeneration catalyst comprises copper, silver, iron, cobalt, manganese, nickel, chromium, vanadium, or a combination thereof.

* * * * *